United States Patent [19]

Meyers et al.

[11] Patent Number: 5,935,582
[45] Date of Patent: Aug. 10, 1999

[54] HOG CHOLERA VIRUS VACCINE AND DIAGNOSTIC

[75] Inventors: Gregor Meyers, Stuttgart, Germany; Tillmann Rümenapf, Pasadena, Calif.; Heinz-Jurgen Thiel, Tübingen, Germany

[73] Assignee: Akzo Nobel, N.V., Arnhem, Netherlands

[21] Appl. No.: 09/059,853

[22] Filed: Apr. 14, 1998

Related U.S. Application Data

[62] Division of application No. 08/873,759, Jun. 12, 1997, Pat. No. 5,811,103, which is a continuation of application No. 08/462,495, Jun. 5, 1995, abandoned, which is a division of application No. 08/123,596, Sep. 20, 1993, abandoned, which is a continuation of application No. 07/797,554, Nov. 22, 1991, abandoned, which is a continuation-in-part of application No. 07/494,991, Mar. 16, 1990, abandoned.

[51] Int. Cl.$^6$ ........................ A61K 39/187; A61K 39/00; C12Q 1/70; G01N 33/53
[52] U.S. Cl. ................................... 424/220.1; 424/184.1; 435/5; 435/7.1; 536/23.1
[58] Field of Search ....................... 424/220.1; 530/350; 435/5, 7.1

[56] References Cited

FOREIGN PATENT DOCUMENTS 0236 977   9/1987   European Pat. Off. .
WO91/00352 1/1991   WIPO .

OTHER PUBLICATIONS

A.L. Fernelius et al., *Can. J. Comp. Med.*, 37:96–102, Jan. 1973.
R. Rümenapf et al., *Virology*, 171:18–27 (1989).
G. Meyers et al., *Virology*, 171:555–567 (1989).
M.C. Collett et al., *J. Gen. Virol.* 70:253–266 (1989).
R.J.M. Moormann et al., *Virus Research,* 11:281–291 (1988).
Collett et al., *Virology,* 165:191–199 (1988).
Collett et al., *Virology,* 165:200–208 (1988).
Declaration of R.J.M. Moorman and enclosures 1–4, re:oral presentation on Dec. 8, 1988.
Thesesis of G. Wensvoort, entitled Epitopes on Structural Proteins of Hog Cholera (Swine Fever) Virus, Mar. 8, 1989, publicly available Mar. 14, 1989.
Dalsgaard et al., *Acta Vet. Scand.*, 17:465–474 (1976).
Renard et al., *DNA*, 4:429–438 (1985).
Geysen et al., *Journal of Immunological Methods,* 102:259–274 (1987).

*Primary Examiner*—Lynette F. Smith
*Attorney, Agent, or Firm*—Mary E. Gormley

[57] ABSTRACT

The present invention is concerned with a hog cholera virus vaccine comprising a polypeptide characteristic of hog cholera virus. Vector vaccines capable to express a nucleic acid sequence encoding such a polypeptide also from part of the present invention. Said polypeptide and nucleic acid sequence can also be used for the detection of hog cholera virus infection.

8 Claims, 2 Drawing Sheets

SEQUENCE LISTING

```
(1) GENERAL INFORMATION:

(iii) NUMBER OF SEQUENCES: 13

(2) INFORMATION FOR SEQ ID NO:1:

(i) SEQUENCE CHARACTERISTICS:
          (A) LENGTH: 12284 base pairs
          (B) TYPE: nucleic acid
          (C) STRANDEDNESS: double
          (D) TOPOLOGY: linear (ii) MOLECULE TYPE: cDNA (vi) ORIGINAL SOURCE:
          (A) ORGANISM: Hog cholera virus
          (B) STRAIN: Alfort
          (H) CELL LINE: PK 15  and 38A1D (ix) FEATURE:
          (A) NAME/KEY: CDS
          (B) LOCATION: 364..12060
          (D) OTHER INFORMATION: /label= 435_kDA_protein (ix) FEATURE:
          (A) NAME/KEY: primer_bind
```

(B) LOCATION: complement (2587..2619)
            (D) OTHER INFORMATION: /label= primer_1

(ix) FEATURE:
            (A) NAME/KEY: primer_bind
            (B) LOCATION: complement (2842..2880)
            (D) OTHER INFORMATION: /label= primer_2

(ix) FEATURE:
            (A) NAME/KEY: variation
            (B) LOCATION: replace(127, "c")

(ix) FEATURE:
            (A) NAME/KEY: variation
            (B) LOCATION: replace(1522, "g")

(ix) FEATURE:
            (A) NAME/KEY: variation
            (B) LOCATION: replace(10989, "t")

(xi) SEQUENCE DESCRIPTION: SEQ ID NO:1:

```
GTTAGCTCTT TCTCGTATAC GATATTGGAT ACACTAAATT TCGATTTGGT CTAGGGCACC         60

CCTCCAGCGA CGGCCGAAAT GGGCTAGCCA TGCCCATAGT AGGACTAGCA AACGGAGGGA        120

CTAGCCGTAG TGGCGAGCTC CCTGGGTGGT CTAAGTCCTG AGTACAGGAC AGTCGTCAGT        180

AGTTCGACGT GAGCACTAGC CCACCTCGAG ATGCTACGTG GACGAGGGCA TGCCCAAGAC        240

ACACCTTAAC CCTGGCGGGG GTCGCTAGGG TGAAATCACA TTATGTGATG GGGGTACGAC        300

CTGATAGGGT GCTGCAGAGG CCCACTAGCA GGCTAGTATA AAAATCTCTG CTGTACATGG        360

CAC ATG GAG TTG AAT CAT TTT GAA TTA TTA TAC AAA ACA AGC AAA CAA         408
    Met Glu Leu Asn His Phe Glu Leu Leu Tyr Lys Thr Ser Lys Gln
      1               5                  10                  15

AAA CCA GTG GGA GTG GAG GAA CCG GTG TAT GAC ACC GCG GGG AGA CCA         456
Lys Pro Val Gly Val Glu Glu Pro Val Tyr Asp Thr Ala Gly Arg Pro
                 20                  25                  30

CTA TTT GGG AAC CCA AGT GAG GTA CAC CCA CAA TCA ACG CTG AAG CTG         504
Leu Phe Gly Asn Pro Ser Glu Val His Pro Gln Ser Thr Leu Lys Leu
             35                  40                  45

CCA CAC GAC AGG GGG AGA GGA GAT ATC AGA ACA ACA CTG AGG GAC CTA         552
Pro His Asp Arg Gly Arg Gly Asp Ile Arg Thr Thr Leu Arg Asp Leu
         50                  55                  60

CCC AGG AAA GGT GAC TGT AGG AGT GGC AAC CAT CTA GGC CCG GTT AGT         600
Pro Arg Lys Gly Asp Cys Arg Ser Gly Asn His Leu Gly Pro Val Ser
     65                  70                  75

GGG ATA TAC ATA AAG CCC GGC CCT GTC TAC TAT CAG GAC TAC ACG GGC         648
Gly Ile Tyr Ile Lys Pro Gly Pro Val Tyr Tyr Gln Asp Tyr Thr Gly
 80                  85                  90                  95

CCA GTC TAT CAC AGA GCT CCT TTA GAG TTC TTT GAT GAG GCC CAG TTC         696
Pro Val Tyr His Arg Ala Pro Leu Glu Phe Phe Asp Glu Ala Gln Phe
                100                 105                 110

TGC GAG GTG ACT AAG AGA ATA GGC AGG GTC ACG GGT AGT GAT GGT AAG         744
Cys Glu Val Thr Lys Arg Ile Gly Arg Val Thr Gly Ser Asp Gly Lys
            115                 120                 125

CTT TAC CAC ATA TAT GTG TGC GTC GAT GGT TGC ATA CTG CTG AAA TTA         792
Leu Tyr His Ile Tyr Val Cys Val Asp Gly Cys Ile Leu Leu Lys Leu
        130                 135                 140

GCC AAA AGG GGC ACA CCC AGA ACC CTA AAG TGG ATT AGG AAC TTC ACC         840
Ala Lys Arg Gly Thr Pro Arg Thr Leu Lys Trp Ile Arg Asn Phe Thr
145                 150                 155

AAC TGT CCA TTA TGG GTA ACC AGT TGC TCC GAT GAC GGC GCA AGT GGC         888
Asn Cys Pro Leu Trp Val Thr Ser Cys Ser Asp Asp Gly Ala Ser Gly
160                 165                 170                 175

AGC AAG GAT AAG AAG CCA GAC AGA ATG AAC AAA GGT AAG TTG AAG ATA         936
Ser Lys Asp Lys Lys Pro Asp Arg Met Asn Lys Gly Lys Leu Lys Ile
```

-continued

```
                         180                  185                   190
GCC CCA AGA GAG CAT GAG AAG GAC AGC AAG ACC AAG CCT CCT GAT GCA        984
Ala Pro Arg Glu His Glu Lys Asp Ser Lys Thr Lys Pro Pro Asp Ala
                195                 200                 205

ACG ATT GTA GTA GAG GGA GTA AAA TAC CAA ATC AAA AAG AAA GGC AAA       1032
Thr Ile Val Val Glu Gly Val Lys Tyr Gln Ile Lys Lys Lys Gly Lys
            210                 215                 220

GTC AAA GGG AAG AAC ACA CAA GAC GGC CTG TAC CAT AAT AAG AAC AAG       1080
Val Lys Gly Lys Asn Thr Gln Asp Gly Leu Tyr His Asn Lys Asn Lys
        225                 230                 235

CCA CCA GAG TCC AGG AAG AAA CTA GAA AAA GCC CTG TTG GCT TGG GCG       1128
Pro Pro Glu Ser Arg Lys Lys Leu Glu Lys Ala Leu Leu Ala Trp Ala
240                 245                 250                 255

GTG ATA ACA ATC TTG CTG TAC CAG CCT GTA GCA GCC GAG AAC ATA ACT       1176
Val Ile Thr Ile Leu Leu Tyr Gln Pro Val Ala Ala Glu Asn Ile Thr
                260                 265                 270

CAA TGG AAC CTG AGT GAC AAC GGC ACT AAT GGT ATT CAG CGA GCC ATG       1224
Gln Trp Asn Leu Ser Asp Asn Gly Thr Asn Gly Ile Gln Arg Ala Met
            275                 280                 285

TAT CTT AGA GGG GTT AAC AGG AGC TTA CAT GGG ATC TGG CCC GAG AAA       1272
Tyr Leu Arg Gly Val Asn Arg Ser Leu His Gly Ile Trp Pro Glu Lys
        290                 295                 300

ATA TGC AAG GGG GTC CCC ACT CAT CTG GCC ACT GAC ACG GAA CTG AAA       1320
Ile Cys Lys Gly Val Pro Thr His Leu Ala Thr Asp Thr Glu Leu Lys
305                 310                 315

GAG ATA CGC GGG ATG ATG GAT GCC AGC GAG AGG ACA AAC TAT ACG TGC       1368
Glu Ile Arg Gly Met Met Asp Ala Ser Glu Arg Thr Asn Tyr Thr Cys
320                 325                 330                 335

TGT AGG TTA CAA AGA CAT GAA TGG AAC AAA CAT GGA TGG TGT AAC TGG       1416
Cys Arg Leu Gln Arg His Glu Trp Asn Lys His Gly Trp Cys Asn Trp
                340                 345                 350

TAC AAC ATA GAC CCT TGG ATT CAG TTA ATG AAC AGG ACC CAA ACA AAT       1464
Tyr Asn Ile Asp Pro Trp Ile Gln Leu Met Asn Arg Thr Gln Thr Asn
            355                 360                 365

TTG ACA GAA GGC CCT CCA GAT AAG GAG TGT GCC GTG ACC TGC AGG TAT       1512
Leu Thr Glu Gly Pro Pro Asp Lys Glu Cys Ala Val Thr Cys Arg Tyr
        370                 375                 380

GAC AAA AAT ACC GAT GTC AAC GTG GTC ACC CAG GCC AGG AAT AGG CCA       1560
Asp Lys Asn Thr Asp Val Asn Val Val Thr Gln Ala Arg Asn Arg Pro
385                 390                 395

ACT ACT CTG ACT GGC TGC AAG AAA GGG AAA AAC TTT TCA TTC GCA GGC       1608
Thr Thr Leu Thr Gly Cys Lys Lys Gly Lys Asn Phe Ser Phe Ala Gly
400                 405                 410                 415

ACA GTC ATA GAG GGC CCG TGC AAT TTC AAC GTT TCC GTG GAG GAC ATC       1656
Thr Val Ile Glu Gly Pro Cys Asn Phe Asn Val Ser Val Glu Asp Ile
                420                 425                 430

TTA TAC GGA GAC CAT GAG TGT GGC AGT CTG CTC CAG GAC ACG GCT CTG       1704
Leu Tyr Gly Asp His Glu Cys Gly Ser Leu Leu Gln Asp Thr Ala Leu
            435                 440                 445

TAC CTA TTG GAT GGA ATG ACC AAC ACT ATA GAG AAT GCC AGG CAA GGT       1752
Tyr Leu Leu Asp Gly Met Thr Asn Thr Ile Glu Asn Ala Arg Gln Gly
        450                 455                 460

GCG GCG CGG GTG ACA TCT TGG CTT GGG AGG CAG CTC AGT ACC GCA GGG       1800
Ala Ala Arg Val Thr Ser Trp Leu Gly Arg Gln Leu Ser Thr Ala Gly
465                 470                 475

AAG AAG CTA GAG AGG AGA AGC AAA ACC TGG TTT GGT GCC TAT GCC CTG       1848
Lys Lys Leu Glu Arg Arg Ser Lys Thr Trp Phe Gly Ala Tyr Ala Leu
480                 485                 490                 495

TCA CCT TAC TGC AAT GTG ACT AGA AAA ATA GGG TAC ATA TGG TAT ACA       1896
Ser Pro Tyr Cys Asn Val Thr Arg Lys Ile Gly Tyr Ile Trp Tyr Thr
```

-continued

```
                500                 505                 510
AAC AAC TGC ACC CCG GCA TGC CTC CCT AAG AAC ACA AAA ATA ATA GGC      1944
Asn Asn Cys Thr Pro Ala Cys Leu Pro Lys Asn Thr Lys Ile Ile Gly
            515                 520                 525

CCT GGA AAG TTT GAC ACC AAT GCG GAA GAC GGG AAG ATC CTT CAT GAA      1992
Pro Gly Lys Phe Asp Thr Asn Ala Glu Asp Gly Lys Ile Leu His Glu
            530                 535                 540

ATG GGG GGC CAC CTA TCA GAA TTT TTG TTG CTT TCT CTA GTT ATC CTG      2040
Met Gly Gly His Leu Ser Glu Phe Leu Leu Leu Ser Leu Val Ile Leu
            545                 550                 555

TCT GAC TTT GCC CCC GAG ACA GCT AGC ACG CTA TAC CTA ATT TTA CAC      2088
Ser Asp Phe Ala Pro Glu Thr Ala Ser Thr Leu Tyr Leu Ile Leu His
560                 565                 570                 575

TAT GCA ATC CCC CAG TCC CAC GAA GAA CCT GAA GGT TGT GAT ACG AAC      2136
Tyr Ala Ile Pro Gln Ser His Glu Glu Pro Glu Gly Cys Asp Thr Asn
            580                 585                 590

CAA CTT AAC CTA ACA GTG AAA CTT AGG ACA GAA GAC GTA GTG CCA TCA      2184
Gln Leu Asn Leu Thr Val Lys Leu Arg Thr Glu Asp Val Val Pro Ser
            595                 600                 605

TCA GTT TGG AAT ATT GGC AAA TAT GTT TGT GTT AGA CCA GAC TGG TGG      2232
Ser Val Trp Asn Ile Gly Lys Tyr Val Cys Val Arg Pro Asp Trp Trp
            610                 615                 620

CCG TAT GAA ACT AAA GTG GCT CTG CTG TTT GAA GAG GCA GGA CAG GTT      2280
Pro Tyr Glu Thr Lys Val Ala Leu Leu Phe Glu Glu Ala Gly Gln Val
625                 630                 635

ATA AAG CTA GTC CTA CGG GCA CTG AGG GAT TTA ACT AGG GTC TGG AAC      2328
Ile Lys Leu Val Leu Arg Ala Leu Arg Asp Leu Thr Arg Val Trp Asn
640                 645                 650                 655

AGC GCA TCA ACT ACT GCG TTT CTC ATT TGC TTG ATA AAA GTA TTG AGA      2376
Ser Ala Ser Thr Thr Ala Phe Leu Ile Cys Leu Ile Lys Val Leu Arg
            660                 665                 670

GGA CAG GTT GTG CAA GGT ATA ATA TGG CTG CTG CTG GTG ACC GGG GCA      2424
Gly Gln Val Val Gln Gly Ile Ile Trp Leu Leu Leu Val Thr Gly Ala
            675                 680                 685

CAA GGG CGG CTA GCC TGT AAG GAA GAC TAC AGG TAT GCG ATC TCG TCA      2472
Gln Gly Arg Leu Ala Cys Lys Glu Asp Tyr Arg Tyr Ala Ile Ser Ser
            690                 695                 700

ACC AAT GAG ATA GGG CTG CTG GGC GCT GAA GGT CTC ACC ACT ACC TGG      2520
Thr Asn Glu Ile Gly Leu Leu Gly Ala Glu Gly Leu Thr Thr Thr Trp
705                 710                 715

AAA GAA TAC AGC CAC GGT TTG CAG CTG GAC GAC GGA ACC GTT AAG GCC      2568
Lys Glu Tyr Ser His Gly Leu Gln Leu Asp Asp Gly Thr Val Lys Ala
720                 725                 730                 735

GTC TGC ACT GCA GGG TCC TTT AAA GTC ACA GCA CTT AAC GTG GTT AGT      2616
Val Cys Thr Ala Gly Ser Phe Lys Val Thr Ala Leu Asn Val Val Ser
            740                 745                 750

AGG AGG TAT CTA GCA TCA TTG CAC AAG AGG GCT CTA CCC ACC TCA GTG      2664
Arg Arg Tyr Leu Ala Ser Leu His Lys Arg Ala Leu Pro Thr Ser Val
            755                 760                 765

ACA TTT GAG CTC CTA TTT GAC GGG ACC AAC CCA GCA ATC GAG GAG ATG      2712
Thr Phe Glu Leu Leu Phe Asp Gly Thr Asn Pro Ala Ile Glu Glu Met
            770                 775                 780

GAT GAT GAC TTC GGA TTT GGG CTG TGC CCA TTT GAC ACG AGT CCT GTG      2760
Asp Asp Asp Phe Gly Phe Gly Leu Cys Pro Phe Asp Thr Ser Pro Val
785                 790                 795

ATC AAA GGG AAG TAC AAC ACC ACT TTG TTA AAC GGC AGT GCT TTC TAT      2808
Ile Lys Gly Lys Tyr Asn Thr Thr Leu Leu Asn Gly Ser Ala Phe Tyr
800                 805                 810                 815

CTA GTC TGC CCA ATA GGA TGG ACT GGT GTC GTA GAG TGC ACA GCA GTG      2856
Leu Val Cys Pro Ile Gly Trp Thr Gly Val Val Glu Cys Thr Ala Val
```

-continued

|  |  |  |  |
|---|---|---|---|
| 820 | 825 | 830 | |

```
AGC CCC ACA ACC TTG AGA ACA GAA GTG GTG AAA ACC TTC AGG AGA GAT      2904
Ser Pro Thr Thr Leu Arg Thr Glu Val Val Lys Thr Phe Arg Arg Asp
        835                 840                 845

AAG CCT TTT CCA CAT AGA GTA GAC TGT GTG ACC ACC ATA GTA GAA AAA      2952
Lys Pro Phe Pro His Arg Val Asp Cys Val Thr Thr Ile Val Glu Lys
        850                 855                 860

GAA GAC CTA TTC CAT TGC AAG TTG GGG GGT AAT TGG ACA TGT GTA AAA      3000
Glu Asp Leu Phe His Cys Lys Leu Gly Gly Asn Trp Thr Cys Val Lys
        865                 870                 875

GGC GAC CCA GTG ACT TAT AAG GGG GGG CAA GTA AAG CAG TGC AGG TGG      3048
Gly Asp Pro Val Thr Tyr Lys Gly Gly Gln Val Lys Gln Cys Arg Trp
880                 885                 890                 895

TGT GGT TTC GAG TTT AAA GAG CCC TAC GGG CTC CCA CAC TAC CCT ATA      3096
Cys Gly Phe Glu Phe Lys Glu Pro Tyr Gly Leu Pro His Tyr Pro Ile
                900                 905                 910

GGC AAG TGC ATC CTA ACA AAT GAG ACA GGT TAC AGG GTA GTA GAT TCC      3144
Gly Lys Cys Ile Leu Thr Asn Glu Thr Gly Tyr Arg Val Val Asp Ser
        915                 920                 925

ACA GAC TGC AAC AGA GAT GGC GTC GTT ATT AGC ACT GAA GGG GAA CAT      3192
Thr Asp Cys Asn Arg Asp Gly Val Val Ile Ser Thr Glu Gly Glu His
        930                 935                 940

GAG TGC TTG ATT GGC AAC ACT ACC GTC AAG GTG CAT GCA CTG GAT GAA      3240
Glu Cys Leu Ile Gly Asn Thr Thr Val Lys Val His Ala Leu Asp Glu
945                 950                 955

AGA TTG GGC CCT ATG CCG TGC AGA CCC AAA GAA ATC GTC TCT AGT GAG      3288
Arg Leu Gly Pro Met Pro Cys Arg Pro Lys Glu Ile Val Ser Ser Glu
960                 965                 970                 975

GGA CCT GTG AGG AAA ACT TCT TGT ACA TTC AAC TAC ACA AAG ACT CTA      3336
Gly Pro Val Arg Lys Thr Ser Cys Thr Phe Asn Tyr Thr Lys Thr Leu
                980                 985                 990

AGA AAC AAA TAC TAT GAG CCC AGA GAC AGT TAC TTC CAG CAA TAT ATG      3384
Arg Asn Lys Tyr Tyr Glu Pro Arg Asp Ser Tyr Phe Gln Gln Tyr Met
        995                 1000                1005

CTC AAG GGC GAG TAT CAA TAC TGG TTT AAT CTG GAC GTG ACC GAC CAC      3432
Leu Lys Gly Glu Tyr Gln Tyr Trp Phe Asn Leu Asp Val Thr Asp His
        1010                1015                1020

CAC ACA GAC TAC TTT GCC GAG TTT GTT GTC TTG GTA GTA GTA GCA CTG      3480
His Thr Asp Tyr Phe Ala Glu Phe Val Val Leu Val Val Val Ala Leu
        1025                1030                1035

TTA GGA GGA AGG TAC GTT CTG TGG CTA ATA GTG ACC TAC ATA ATT CTA      3528
Leu Gly Gly Arg Tyr Val Leu Trp Leu Ile Val Thr Tyr Ile Ile Leu
1040                1045                1050                1055

ACA GAG CAG CTC GCT GCT GGT CTA CAG CTA GGC CAG GGT GAG GTG GTA      3576
Thr Glu Gln Leu Ala Ala Gly Leu Gln Leu Gly Gln Gly Glu Val Val
                1060                1065                1070

TTG ATA GGG AAC CTA ATT ACC CAC ACG GAC AAT GAG GTG GTG GTG TAC      3624
Leu Ile Gly Asn Leu Ile Thr His Thr Asp Asn Glu Val Val Val Tyr
        1075                1080                1085

TTC CTA CTG CTC TAC TTA GTA ATA AGA GAT GAG CCC ATA AAG AAA TGG      3672
Phe Leu Leu Leu Tyr Leu Val Ile Arg Asp Glu Pro Ile Lys Lys Trp
        1090                1095                1100

ATA CTA CTG CTG TTT CAT GCA ATG ACT AAC AAT CCA GTC AAG ACC ATA      3720
Ile Leu Leu Leu Phe His Ala Met Thr Asn Asn Pro Val Lys Thr Ile
        1105                1110                1115

ACA GTA GCA TTG CTA ATG ATC AGT GGG GTT GCC AAG GGT GGT AAG ATA      3768
Thr Val Ala Leu Leu Met Ile Ser Gly Val Ala Lys Gly Gly Lys Ile
1120                1125                1130                1135

GAT GGT GGC TGG CAG AGA CAA CCG GTG ACC AGT TTT GAC ATC CAA CTC      3816
Asp Gly Gly Trp Gln Arg Gln Pro Val Thr Ser Phe Asp Ile Gln Leu
```

-continued

```
                    1140                1145                 1150
GCA CTG GCA GTC GTA GTA GTC GTT GTG ATG TTG CTG GCA AAG AGA GAC   3864
Ala Leu Ala Val Val Val Val Val Val Met Leu Leu Ala Lys Arg Asp
             1155                1160                1165

CCG ACT ACT TTC CCT TTG GTA ATC ACA GTG GCA ACC CTG AGA ACG GCC   3912
Pro Thr Thr Phe Pro Leu Val Ile Thr Val Ala Thr Leu Arg Thr Ala
             1170                1175                1180

AAG ATA ACC AAC GGT TTT AGC ACA GAT CTA GTC ATA GCC ACA GTG TCG   3960
Lys Ile Thr Asn Gly Phe Ser Thr Asp Leu Val Ile Ala Thr Val Ser
             1185                1190                1195

GCA GCT TTG TTA ACT TGG ACC TAT ATC AGC GAC TAC TAC AAA TAC AAG   4008
Ala Ala Leu Leu Thr Trp Thr Tyr Ile Ser Asp Tyr Tyr Lys Tyr Lys
1200                1205                1210                1215

ACT TGG CTA CAG TAC CTC GTC AGC ACG GTG ACT GGA ATC TTC CTG ATA   4056
Thr Trp Leu Gln Tyr Leu Val Ser Thr Val Thr Gly Ile Phe Leu Ile
             1220                1225                1230

AGG GTG CTG AAG GGA ATA GGC GAA TTG GAT CTG CAC GCC CCA ACC TTG   4104
Arg Val Leu Lys Gly Ile Gly Glu Leu Asp Leu His Ala Pro Thr Leu
             1235                1240                1245

CCG TCT CAC AGA CCC CTC TTT TAC ATC CTT GTA TAC CTT ATT TCC ACT   4152
Pro Ser His Arg Pro Leu Phe Tyr Ile Leu Val Tyr Leu Ile Ser Thr
             1250                1255                1260

GCC GTG GTA ACT AGA TGG AAT CTG GAC GTA GCC GGA TTG TTG CTG CAG   4200
Ala Val Val Thr Arg Trp Asn Leu Asp Val Ala Gly Leu Leu Leu Gln
             1265                1270                1275

TGC GTC CCA ACT CTT TTA ATG GTT TTT ACG ATG TGG GCA GAC ATT CTC   4248
Cys Val Pro Thr Leu Leu Met Val Phe Thr Met Trp Ala Asp Ile Leu
1280                1285                1290                1295

ACC CTA ATT CTC ATA CTA CCT ACT TAT GAG TTA ACA AAG TTA TAC TAC   4296
Thr Leu Ile Leu Ile Leu Pro Thr Tyr Glu Leu Thr Lys Leu Tyr Tyr
             1300                1305                1310

CTT AAG GAA GTG AAG ATT GGG GCA GAA AGA GGT TGG CTG TGG AAA ACT   4344
Leu Lys Glu Val Lys Ile Gly Ala Glu Arg Gly Trp Leu Trp Lys Thr
             1315                1320                1325

AAC TAT AAG AGG GTA AAC GAC ATC TAC GAG GTC GAC CAA ACT AGC GAA   4392
Asn Tyr Lys Arg Val Asn Asp Ile Tyr Glu Val Asp Gln Thr Ser Glu
             1330                1335                1340

GGG GTT TAC CTT TTC CCT TCT AAA CAG AGG ACG AGC GCT ATA ACT AGT   4440
Gly Val Tyr Leu Phe Pro Ser Lys Gln Arg Thr Ser Ala Ile Thr Ser
1345                1350                1355

ACC ATG TTG CCA TTA ATC AAA GCC ATA CTC ATT AGC TGC ATC AGC AAC   4488
Thr Met Leu Pro Leu Ile Lys Ala Ile Leu Ile Ser Cys Ile Ser Asn
1360                1365                1370                1375

AAG TGG CAA CTC ATA TAC TTA CTG TAC TTG ATA TTT GAA GTG TCT TAC   4536
Lys Trp Gln Leu Ile Tyr Leu Leu Tyr Leu Ile Phe Glu Val Ser Tyr
             1380                1385                1390

TAC CTC CAC AAG AAA GTT ATA GAT GAA ATA GCT GGT GGG ACC AAC TTC   4584
Tyr Leu His Lys Lys Val Ile Asp Glu Ile Ala Gly Gly Thr Asn Phe
             1395                1400                1405

GTT TCA AGG CTC GTG GCG GCT TTG ATT GAA GTC AAT TGG GCC TTC GAC   4632
Val Ser Arg Leu Val Ala Ala Leu Ile Glu Val Asn Trp Ala Phe Asp
             1410                1415                1420

AAT GAA GAA GTC AAA GGC TTA AAG AAG TTC TTC TTG CTG TCT AGT AGG   4680
Asn Glu Glu Val Lys Gly Leu Lys Lys Phe Phe Leu Leu Ser Ser Arg
             1425                1430                1435

GTC AAA GAG TTG ATC ATC AAA CAC AAA GTG AGG AAT GAA GTA GTG GTC   4728
Val Lys Glu Leu Ile Ile Lys His Lys Val Arg Asn Glu Val Val Val
1440                1445                1450                1455

CGC TGG TTT GGA GAT GAA GAG ATT TAT GGG ATG CCA AAG CTG ATC GGC   4776
Arg Trp Phe Gly Asp Glu Glu Ile Tyr Gly Met Pro Lys Leu Ile Gly
```

-continued

```
                  1460                1465                1470
TTA GTT AAG GCA GCA ACA CTA AGT AGA AAC AAA CAC TGT ATG TTG TGT    4824
Leu Val Lys Ala Ala Thr Leu Ser Arg Asn Lys His Cys Met Leu Cys
            1475                1480                1485

ACC GTC TGT GAG GAC AGA GAT TGG AGA GGG GAA ACT TGC CCT AAA TGT    4872
Thr Val Cys Glu Asp Arg Asp Trp Arg Gly Glu Thr Cys Pro Lys Cys
            1490                1495                1500

GGG CGT TTT GGA CCA CCA GTG GTC TGC GGT ATG ACC CTA GCC GAT TTC    4920
Gly Arg Phe Gly Pro Pro Val Val Cys Gly Met Thr Leu Ala Asp Phe
        1505                1510                1515

GAA GAA AAA CAC TAT AAA AGG ATT TTC ATT AGA GAG GAC CAA TCA GGC    4968
Glu Glu Lys His Tyr Lys Arg Ile Phe Ile Arg Glu Asp Gln Ser Gly
1520                1525                1530                1535

GGG CCA CTT AGG GAG GAG CAT GCA GGG TAC TTG CAG TAC AAA GCC AGG    5016
Gly Pro Leu Arg Glu Glu His Ala Gly Tyr Leu Gln Tyr Lys Ala Arg
            1540                1545                1550

GGT CAA CTG TTT TTG AGG AAC CTC CCA GTG TTA GCT ACA AAA GTC AAG    5064
Gly Gln Leu Phe Leu Arg Asn Leu Pro Val Leu Ala Thr Lys Val Lys
            1555                1560                1565

ATG CTC CTG GTT GGT AAC CTC GGG ACA GAG ATT GGG GAT CTG GAA CAC    5112
Met Leu Leu Val Gly Asn Leu Gly Thr Glu Ile Gly Asp Leu Glu His
            1570                1575                1580

CTT GGC TGG GTG CTT AGA GGG CCA GCT GTT TGC AAG AAG GTT ACT GAA    5160
Leu Gly Trp Val Leu Arg Gly Pro Ala Val Cys Lys Lys Val Thr Glu
            1585                1590                1595

CAC GAA AGA TGC ACC ACG TCT ATA ATG GAT AAG TTG ACT GCT TTC TTT    5208
His Glu Arg Cys Thr Thr Ser Ile Met Asp Lys Leu Thr Ala Phe Phe
1600                1605                1610                1615

GGA GTA ATG CCA AGG GGC ACT ACT CCC AGA GCT CCC GTA AGA TTC CCT    5256
Gly Val Met Pro Arg Gly Thr Thr Pro Arg Ala Pro Val Arg Phe Pro
            1620                1625                1630

ACC TCC CTC CTA AAG ATA AGA AGA GGG CTG GAG ACT GGT TGG GCT TAC    5304
Thr Ser Leu Leu Lys Ile Arg Arg Gly Leu Glu Thr Gly Trp Ala Tyr
            1635                1640                1645

ACA CAC CAA GGT GGC ATC AGC TCA GTA GAC CAT GTC ACT TGT GGG AAA    5352
Thr His Gln Gly Gly Ile Ser Ser Val Asp His Val Thr Cys Gly Lys
            1650                1655                1660

GAC TTA CTG GTG TGT GAC ACC ATG GGT CGG ACA AGG GTT GTT TGC CAG    5400
Asp Leu Leu Val Cys Asp Thr Met Gly Arg Thr Arg Val Val Cys Gln
            1665                1670                1675

TCA AAT AAT AAG ATG ACC GAC GAG TCC GAA TAC GGA GTC AAA ACT GAC    5448
Ser Asn Asn Lys Met Thr Asp Glu Ser Glu Tyr Gly Val Lys Thr Asp
1680                1685                1690                1695

TCC GGG TGC CCA GAG GGA GCC AGG TGT TAC GTG TTT AAC CCG GAA GCA    5496
Ser Gly Cys Pro Glu Gly Ala Arg Cys Tyr Val Phe Asn Pro Glu Ala
            1700                1705                1710

GTT AAC ATA TCA GGC ACT AAA GGA GCC ATG GTC CAC TTA CAG AAA ACG    5544
Val Asn Ile Ser Gly Thr Lys Gly Ala Met Val His Leu Gln Lys Thr
            1715                1720                1725

GGT GGA GAA TTC ACC TGT GTG ACA GCA TCA GGA ACC CCG GCC TTC TTT    5592
Gly Gly Glu Phe Thr Cys Val Thr Ala Ser Gly Thr Pro Ala Phe Phe
            1730                1735                1740

GAC CTC AAG AAC CTT AAG GGC TGG TCA GGG CTA CCG ATA TTT GAA GCA    5640
Asp Leu Lys Asn Leu Lys Gly Trp Ser Gly Leu Pro Ile Phe Glu Ala
            1745                1750                1755

TCA AGT GGA AGG GTA GTC GGA AGG GTC AAG GTC GGG AAG AAC GAG GAT    5688
Ser Ser Gly Arg Val Val Gly Arg Val Lys Val Gly Lys Asn Glu Asp
1760                1765                1770                1775

TCC AAA CCA ACC AAG CTC ATG AGT GGG ATA CAA ACG GTT TCT AAA AGC    5736
Ser Lys Pro Thr Lys Leu Met Ser Gly Ile Gln Thr Val Ser Lys Ser
```

-continued

```
                1780                1785                1790
GCC ACA GAC TTG ACG GAG ATG GTG AAG AAG ATA ACG ACC ATG AAC AGG       5784
Ala Thr Asp Leu Thr Glu Met Val Lys Lys Ile Thr Thr Met Asn Arg
            1795                1800                1805

GGA GAG TTC AGA CAA ATA ACC CTG GCC ACA GGT GCC GGA AAA ACT ACA       5832
Gly Glu Phe Arg Gln Ile Thr Leu Ala Thr Gly Ala Gly Lys Thr Thr
        1810                1815                1820

GAG CTC CCT AGA TCA GTT ATA GAA GAG ATA GGG AGG CAT AAG AGG GTG       5880
Glu Leu Pro Arg Ser Val Ile Glu Glu Ile Gly Arg His Lys Arg Val
    1825                1830                1835

TTG GTC TTA ATC CCC TTG AGG GCG GCA GCA GAA TCA GTA TAC CAA TAC       5928
Leu Val Leu Ile Pro Leu Arg Ala Ala Ala Glu Ser Val Tyr Gln Tyr
1840                1845                1850                1855

ATG AGA CAG AAA CAT CCG AGT ATA GCA TTC AAT CTA AGG ATA GGT GAG       5976
Met Arg Gln Lys His Pro Ser Ile Ala Phe Asn Leu Arg Ile Gly Glu
        1860                1865                1870

ATG AAG GAA GGT GAT ATG GCC ACG GGA ATA ACC TAT GCC TCT TAC GGT       6024
Met Lys Glu Gly Asp Met Ala Thr Gly Ile Thr Tyr Ala Ser Tyr Gly
    1875                1880                1885

TAC TTT TGC CAG ATG TCA CAA CCC AAG CTG AGA GCC GCA ATG GTA GAA       6072
Tyr Phe Cys Gln Met Ser Gln Pro Lys Leu Arg Ala Ala Met Val Glu
1890                1895                1900

TAT TCC TTT ATA TTC CTA GAT GAG TAT CAT TGT GCT ACC CCA GAA CAA       6120
Tyr Ser Phe Ile Phe Leu Asp Glu Tyr His Cys Ala Thr Pro Glu Gln
        1905                1910                1915

CTG GCA ATC ATG GGG AAG ATC CAC AGA TTC TCA GAA AAC CTG CGG GTG       6168
Leu Ala Ile Met Gly Lys Ile His Arg Phe Ser Glu Asn Leu Arg Val
1920                1925                1930                1935

GTA GCT ATG ACA GCG ACA CCG GCA GGC ACA GTA ACA ACT ACT GGG CAG       6216
Val Ala Met Thr Ala Thr Pro Ala Gly Thr Val Thr Thr Thr Gly Gln
            1940                1945                1950

AAA CAC CCT ATA GAG GAA TTT ATA GCC CCG GAA GTG ATG AAA GGA GAA       6264
Lys His Pro Ile Glu Glu Phe Ile Ala Pro Glu Val Met Lys Gly Glu
        1955                1960                1965

GAC TTG GGT TCT GAG TAC TTA GAT ATT GCC GGA CTG AAG ATA CCA GTA       6312
Asp Leu Gly Ser Glu Tyr Leu Asp Ile Ala Gly Leu Lys Ile Pro Val
    1970                1975                1980

GAG GAG ATG AAG AAT AAC ATG CTA GTT TTT GTG CCC ACC AGG AAC ATG       6360
Glu Glu Met Lys Asn Asn Met Leu Val Phe Val Pro Thr Arg Asn Met
        1985                1990                1995

GCG GTA GAG GCG GCA AAG AAA TTG AAG GCC AAA GGA TAC AAC TCG GGC       6408
Ala Val Glu Ala Ala Lys Lys Leu Lys Ala Lys Gly Tyr Asn Ser Gly
2000                2005                2010                2015

TAC TAC TAC AGC GGA GAG GAC CCA TCT AAC CTG AGG GTG GTG ACG TCG       6456
Tyr Tyr Tyr Ser Gly Glu Asp Pro Ser Asn Leu Arg Val Val Thr Ser
            2020                2025                2030

CAG TCC CCA TAC GTG GTG GTA GCA ACC AAC GCA ATA GAA TCG GGC GTT       6504
Gln Ser Pro Tyr Val Val Val Ala Thr Asn Ala Ile Glu Ser Gly Val
        2035                2040                2045

ACC CTC CCG GAC CTG GAC GTG GTT GTC GAC ACG GGA CTC AAG TGT GAA       6552
Thr Leu Pro Asp Leu Asp Val Val Val Asp Thr Gly Leu Lys Cys Glu
    2050                2055                2060

AAA AGA ATC CGA CTG TCA CCC AAG ATG CCT TTC ATA GTG ACG GGC CTG       6600
Lys Arg Ile Arg Leu Ser Pro Lys Met Pro Phe Ile Val Thr Gly Leu
        2065                2070                2075

AAA AGA ATG GCC GTC ACT ATT GGG GAA CAA GCC CAG AGA AGA GGG AGG       6648
Lys Arg Met Ala Val Thr Ile Gly Glu Gln Ala Gln Arg Arg Gly Arg
2080                2085                2090                2095

GTT GGA AGA GTG AAG CCC GGG AGA TAC TAC AGG AGT CAA GAA ACA CCT       6696
Val Gly Arg Val Lys Pro Gly Arg Tyr Tyr Arg Ser Gln Glu Thr Pro
```

-continued

```
                   2100              2105              2110
GTC GGC TCT AAA GAC TAC CAT TAT GAC TTA TTG CAA GCC CAG AGG TAC      6744
Val Gly Ser Lys Asp Tyr His Tyr Asp Leu Leu Gln Ala Gln Arg Tyr
            2115              2120              2125

GGC ATA GAA GAT GGG ATA AAT ATC ACC AAA TCC TTC AGA GAG ATG AAC      6792
Gly Ile Glu Asp Gly Ile Asn Ile Thr Lys Ser Phe Arg Glu Met Asn
            2130              2135              2140

TAC GAC TGG AGC CTT TAT GAG GAA GAT AGC CTG ATG ATC ACA CAA CTG      6840
Tyr Asp Trp Ser Leu Tyr Glu Glu Asp Ser Leu Met Ile Thr Gln Leu
            2145              2150              2155

GAA ATC CTC AAC AAC CTG TTG ATA TCA GAA GAG CTG CCG ATG GCA GTA      6888
Glu Ile Leu Asn Asn Leu Leu Ile Ser Glu Glu Leu Pro Met Ala Val
2160              2165              2170              2175

AAA AAT ATA ATG GCC AGG ACC GAC CAC CCA GAA CCA ATT CAA CTC GCG      6936
Lys Asn Ile Met Ala Arg Thr Asp His Pro Glu Pro Ile Gln Leu Ala
            2180              2185              2190

TAT AAC AGC TAC GAG ACA CAG GTG CCG GTA TTA TTC CCA AAA ATA AGA      6984
Tyr Asn Ser Tyr Glu Thr Gln Val Pro Val Leu Phe Pro Lys Ile Arg
            2195              2200              2205

AAT GGA GAG GTG ACT GAT ACT TAC GAT AAT TAC ACC TTC CTC AAT GCA      7032
Asn Gly Glu Val Thr Asp Thr Tyr Asp Asn Tyr Thr Phe Leu Asn Ala
            2210              2215              2220

AGA AAA TTG GGA GAT GAC GTA CCC CCC TAC GTG TAT GCT ACA GAG GAT      7080
Arg Lys Leu Gly Asp Asp Val Pro Pro Tyr Val Tyr Ala Thr Glu Asp
2225              2230              2235

GAG GAC TTG GCA GTG GAA CTG TTG GGC CTA GAT TGG CCG GAC CCA GGA      7128
Glu Asp Leu Ala Val Glu Leu Leu Gly Leu Asp Trp Pro Asp Pro Gly
2240              2245              2250              2255

AAC CAA GGC ACC GTG GAA GCT GGC AGA GCA CTA AAA CAG GTG GTT GGT      7176
Asn Gln Gly Thr Val Glu Ala Gly Arg Ala Leu Lys Gln Val Val Gly
            2260              2265              2270

CTA TCA ACA GCA GAG AAC GCC CTG CTA GTC GCC CTG TTC GGC TAC GTG      7224
Leu Ser Thr Ala Glu Asn Ala Leu Leu Val Ala Leu Phe Gly Tyr Val
            2275              2280              2285

GGG TAC CAG GCG CTT TCA AAG AGA CAT ATA CCA GTG GTC ACA GAT ATA      7272
Gly Tyr Gln Ala Leu Ser Lys Arg His Ile Pro Val Val Thr Asp Ile
            2290              2295              2300

TAT TCA GTA GAA GAT CAC AGG CTA GAG GAC ACT ACG CAC CTA CAG TAT      7320
Tyr Ser Val Glu Asp His Arg Leu Glu Asp Thr Thr His Leu Gln Tyr
            2305              2310              2315

GCT CCG AAT GCC ATC AAG ACG GAG GGG AAG GAA ACT GAA TTG AAG GAG      7368
Ala Pro Asn Ala Ile Lys Thr Glu Gly Lys Glu Thr Glu Leu Lys Glu
2320              2325              2330              2335

CTG GCT CAG GGG GAT GTG CAG AGA TGT GTG GAA GCA GTG ACC AAT TAT      7416
Leu Ala Gln Gly Asp Val Gln Arg Cys Val Glu Ala Val Thr Asn Tyr
            2340              2345              2350

GCG AGA GAG GGC ATC CAA TTC ATG AAG TCG CAG GCA CTG AAA GTG AGA      7464
Ala Arg Glu Gly Ile Gln Phe Met Lys Ser Gln Ala Leu Lys Val Arg
            2355              2360              2365

GAA ACC CCT ACC TAT AAA GAG ACA ATG AAC ACC GTG GCA GAT TAT GTG      7512
Glu Thr Pro Thr Tyr Lys Glu Thr Met Asn Thr Val Ala Asp Tyr Val
            2370              2375              2380

AAA AAG TTT ATT GAG GCA CTG ACG GAT AGC AAG GAA GAC ATC ATT AAA      7560
Lys Lys Phe Ile Glu Ala Leu Thr Asp Ser Lys Glu Asp Ile Ile Lys
            2385              2390              2395

TAT GGG CTG TGG GGG GCA CAT ACG GCA TTG TAT AAG AGC ATT GGT GCC      7608
Tyr Gly Leu Trp Gly Ala His Thr Ala Leu Tyr Lys Ser Ile Gly Ala
2400              2405              2410              2415

AGG CTT GGT CAC GAA ACC GCG TTC GCA ACT CTA GTT GTG AAG TGG TTG      7656
Arg Leu Gly His Glu Thr Ala Phe Ala Thr Leu Val Val Lys Trp Leu
```

-continued

```
                  2420                 2425                2430
GCA TTT GGG GGG GAG TCA ATA TCA GAC CAC ATA AAG CAA GCG GCC ACA      7704
Ala Phe Gly Gly Glu Ser Ile Ser Asp His Ile Lys Gln Ala Ala Thr
                2435                2440                2445

GAC TTG GTC GTT TAT TAC ATT ATT AAC AGA CCT CAA TTC CCA GGA GAC      7752
Asp Leu Val Val Tyr Tyr Ile Ile Asn Arg Pro Gln Phe Pro Gly Asp
                2450                2455                2460

ACA GAA ACA CAA CAA GAA GGG AGA AAA TTT GTT GCC AGC CTG CTA GTC      7800
Thr Glu Thr Gln Gln Glu Gly Arg Lys Phe Val Ala Ser Leu Leu Val
                2465                2470                2475

TCA GCT CTA GCG ACT TAT ACA TAC AAG AGC TGG AAC TAC AAT AAT CTG      7848
Ser Ala Leu Ala Thr Tyr Thr Tyr Lys Ser Trp Asn Tyr Asn Asn Leu
2480                2485                2490                2495

TCC AAA ATA GTT GAA CCG GCT TTG GCT ACC CTG CCC TAT GCC GCT AAA      7896
Ser Lys Ile Val Glu Pro Ala Leu Ala Thr Leu Pro Tyr Ala Ala Lys
                2500                2505                2510

GCC CTC AAG CTA TTT GCT CCT ACC CGA CTG GAG AGC GTT GTC ATA CTG      7944
Ala Leu Lys Leu Phe Ala Pro Thr Arg Leu Glu Ser Val Val Ile Leu
                2515                2520                2525

AGC ACT GCA ATC TAC AAA ACA TAC CTA TCA ATA AGG CGA GGC AAA AGT      7992
Ser Thr Ala Ile Tyr Lys Thr Tyr Leu Ser Ile Arg Arg Gly Lys Ser
                2530                2535                2540

GAT GGT CTG CTA GGT ACA GGG GTT AGC GCG GCC ATG GAA ATT ATG TCA      8040
Asp Gly Leu Leu Gly Thr Gly Val Ser Ala Ala Met Glu Ile Met Ser
                2545                2550                2555

CAA AAC CCA GTA TCT GTG GGT ATA GCA GTT ATG CTA GGG GTA GGG GCT      8088
Gln Asn Pro Val Ser Val Gly Ile Ala Val Met Leu Gly Val Gly Ala
2560                2565                2570                2575

GTA GCA GCC CAC AAT GCA ATT GAA GCC AGT GAG CAA AAA AGA ACA CTA      8136
Val Ala Ala His Asn Ala Ile Glu Ala Ser Glu Gln Lys Arg Thr Leu
                2580                2585                2590

CTT ATG AAA GTC TTT GTG AAA AAC TTC TTA GAC CAG GCC GCC ACC GAC      8184
Leu Met Lys Val Phe Val Lys Asn Phe Leu Asp Gln Ala Ala Thr Asp
                2595                2600                2605

GAA CTA GTC AAA GAG AGC CCT GAG AAA ATA ATA ATG GCT TTG TTC GAA      8232
Glu Leu Val Lys Glu Ser Pro Glu Lys Ile Ile Met Ala Leu Phe Glu
                2610                2615                2620

GCG GTG CAA ACG GTG GGC AAC CCT CTT AGA TTA GTG TAC CAC CTC TAT      8280
Ala Val Gln Thr Val Gly Asn Pro Leu Arg Leu Val Tyr His Leu Tyr
                2625                2630                2635

GGA GTT TTC TAT AAA GGG TGG GAA GCA AAA GAG TTG GCC CAA AGA ACA      8328
Gly Val Phe Tyr Lys Gly Trp Glu Ala Lys Glu Leu Ala Gln Arg Thr
2640                2645                2650                2655

GCC GGC AGG AAC CTT TTC ACC TTG ATA ATG TTC GAG GCT GTG GAA CTA      8376
Ala Gly Arg Asn Leu Phe Thr Leu Ile Met Phe Glu Ala Val Glu Leu
                2660                2665                2670

CTG GGA GTA GAC AGT GAG GGA AAA ATT CGC CAG CTA TCG AGC AAT TAC      8424
Leu Gly Val Asp Ser Glu Gly Lys Ile Arg Gln Leu Ser Ser Asn Tyr
                2675                2680                2685

ATA CTA GAG CTC TTG TAT AAG TTC CGC GAC AAT ATC AAG TCT AGT GTG      8472
Ile Leu Glu Leu Leu Tyr Lys Phe Arg Asp Asn Ile Lys Ser Ser Val
                2690                2695                2700

AGG GAG ATA GCA ATC AGC TGG GCC CCC GCC CCC TTT AGT TGC GAT TGG      8520
Arg Glu Ile Ala Ile Ser Trp Ala Pro Ala Pro Phe Ser Cys Asp Trp
                2705                2710                2715

ACA CCA ACA GAT GAC AGA ATA GGG CTT CCC CAT GAC AAT TAC CTC CGA      8568
Thr Pro Thr Asp Asp Arg Ile Gly Leu Pro His Asp Asn Tyr Leu Arg
2720                2725                2730                2735

GTG GAG ACA AAG TGC CCC TGT GGT TAC AGG ATG AAA GCG GTA AAA AAC      8616
Val Glu Thr Lys Cys Pro Cys Gly Tyr Arg Met Lys Ala Val Lys Asn
```

-continued

```
                   2740              2745              2750
TGC GCT GGG GAG TTG AGA CTT CTG GAG GAA GGG GGT TCA TTC CTC TGC    8664
Cys Ala Gly Glu Leu Arg Leu Leu Glu Glu Gly Gly Ser Phe Leu Cys
            2755              2760              2765

AGA AAT AAA TTC GGT AGA GGC TCA CAA AAC TAC AGG GTG ACA AAA TAC    8712
Arg Asn Lys Phe Gly Arg Gly Ser Gln Asn Tyr Arg Val Thr Lys Tyr
        2770              2775              2780

TAT GAT GAC AAT TTA TCA GAA ATA AAA CCA GTG ATA AGA ATG GAA GGA    8760
Tyr Asp Asp Asn Leu Ser Glu Ile Lys Pro Val Ile Arg Met Glu Gly
        2785              2790              2795

CAC GTG GAA CTG TAT TAC AAG GGG GCC ACT ATC AAA CTG GAT TTT AAC    8808
His Val Glu Leu Tyr Tyr Lys Gly Ala Thr Ile Lys Leu Asp Phe Asn
2800              2805              2810              2815

AAC AGT AAA ACG GTA CTG GCA ACT GAC AAA TGG GAG GTT GAC CAC TCC    8856
Asn Ser Lys Thr Val Leu Ala Thr Asp Lys Trp Glu Val Asp His Ser
            2820              2825              2830

ACC CTG GTT AGG GCA CTC AAG AGG TAC ACA GGG GCT GGA TAT CGA GGG    8904
Thr Leu Val Arg Ala Leu Lys Arg Tyr Thr Gly Ala Gly Tyr Arg Gly
        2835              2840              2845

GCG TAT TTG GGT GAG AAA CCT AAC CAT AAA CAT CTG ATA CAG AGA GAC    8952
Ala Tyr Leu Gly Glu Lys Pro Asn His Lys His Leu Ile Gln Arg Asp
        2850              2855              2860

TGT GCA ACG ATT ACC AAA GAC AAG GTC TGC TTC ATC AAA ATG AAG AGA    9000
Cys Ala Thr Ile Thr Lys Asp Lys Val Cys Phe Ile Lys Met Lys Arg
        2865              2870              2875

GGG TGT GCG TTC ACT TAT GAC CTA TCC CTC CAC AAC CTT ACC CGG CTA    9048
Gly Cys Ala Phe Thr Tyr Asp Leu Ser Leu His Asn Leu Thr Arg Leu
2880              2885              2890              2895

ATC GAA TTG GTA CAC AAG AAT AAC CTG GAA GAT AGA GAA ATC CCT GCT    9096
Ile Glu Leu Val His Lys Asn Asn Leu Glu Asp Arg Glu Ile Pro Ala
            2900              2905              2910

GTG ACG GTT ACA ACC TGG CTG GCC TAC ACA TTT GTG AAT GAA GAC ATA    9144
Val Thr Val Thr Thr Trp Leu Ala Tyr Thr Phe Val Asn Glu Asp Ile
        2915              2920              2925

GGG ACC ATA AAA CCA ACT TTT GGG GAA AAG GTG ACA CCG GAG AAA CAG    9192
Gly Thr Ile Lys Pro Thr Phe Gly Glu Lys Val Thr Pro Glu Lys Gln
        2930              2935              2940

GAG GAG GTA GTC TTG CAG CCT GCT GTG GTG GTG GAC ACA ACA GAT GTA    9240
Glu Glu Val Val Leu Gln Pro Ala Val Val Val Asp Thr Thr Asp Val
        2945              2950              2955

GCC GTG ACC GTG GTA GGG GAA ACC TCT ACT ATG ACT ACA GGG GAG ACC    9288
Ala Val Thr Val Val Gly Glu Thr Ser Thr Met Thr Thr Gly Glu Thr
2960              2965              2970              2975

CCG ACA ACA TTT ACC AGC TTA GGT TCG GAC TCG AAG GTC CGA CAA GTC    9336
Pro Thr Thr Phe Thr Ser Leu Gly Ser Asp Ser Lys Val Arg Gln Val
        2980              2985              2990

CTG AAG CTG GGC GTG GAC GAT GGT CAA TAC CCC GGG CCT AAT CAG CAG    9384
Leu Lys Leu Gly Val Asp Asp Gly Gln Tyr Pro Gly Pro Asn Gln Gln
        2995              3000              3005

AGA GCA AGC CTG CTC GAA GCT ATA CAA GGT GTG GAT GAA AGG CCC TCG    9432
Arg Ala Ser Leu Leu Glu Ala Ile Gln Gly Val Asp Glu Arg Pro Ser
        3010              3015              3020

GTA CTG ATA CTG GGG TCT GAT AAG GCC ACC TCC AAT AGG GTC AAG ACC    9480
Val Leu Ile Leu Gly Ser Asp Lys Ala Thr Ser Asn Arg Val Lys Thr
        3025              3030              3035

GCA AAG AAT GTG AAG ATA TAT AGG AGC AGG GAC CCC CTG GAA CTG AGA    9528
Ala Lys Asn Val Lys Ile Tyr Arg Ser Arg Asp Pro Leu Glu Leu Arg
3040              3045              3050              3055

GAA ATG ATG AAA AGG GGA AAA ATC CTA GTC GTA GCC TTG TCT AGA GTC    9576
Glu Met Met Lys Arg Gly Lys Ile Leu Val Val Ala Leu Ser Arg Val
```

```
                 3060               3065              3070
GAT ACC GCT CTG CTG AAA TTC GTT GAT TAC AAA GGC ACC TTC CTG ACC    9624
Asp Thr Ala Leu Leu Lys Phe Val Asp Tyr Lys Gly Thr Phe Leu Thr
             3075              3080             3085

AGA GAG ACC CTA GAG GCA TTA AGT CTG GGT AAG CCT AAG AAA AGA GAC    9672
Arg Glu Thr Leu Glu Ala Leu Ser Leu Gly Lys Pro Lys Lys Arg Asp
         3090              3095              3100

ATA ACT AAA GCA GAA GCA CAA TGG CTG CTG CGC CTC GAA GAC CAA ATA    9720
Ile Thr Lys Ala Glu Ala Gln Trp Leu Leu Arg Leu Glu Asp Gln Ile
         3105              3110              3115

GAA GAG CTG CCT GAC TGG TTC GCA GCC AAG GAA CCC ATA TTT CTA GAA    9768
Glu Glu Leu Pro Asp Trp Phe Ala Ala Lys Glu Pro Ile Phe Leu Glu
3120             3125              3130             3135

GCC AAC ATT AAA CGT GAC AAG TAT CAC CTG GTA GGG GAC ATA GCC ACT    9816
Ala Asn Ile Lys Arg Asp Lys Tyr His Leu Val Gly Asp Ile Ala Thr
             3140              3145              3150

ATT AAA GAA AAA GCC AAA CAA CTG GGG GCA ACA GAC TCC ACA AAG ATA    9864
Ile Lys Glu Lys Ala Lys Gln Leu Gly Ala Thr Asp Ser Thr Lys Ile
             3155              3160              3165

TCA AAG GAG GTT GGC GCG AAA GTG TAT TCT ATG AAG CTG AGT AAC TGG    9912
Ser Lys Glu Val Gly Ala Lys Val Tyr Ser Met Lys Leu Ser Asn Trp
         3170              3175              3180

GTG ATA CAA GAA GAG AAT AAA CAA GGC AGC CTT GCC CCC CTG TTT GAA    9960
Val Ile Gln Glu Glu Asn Lys Gln Gly Ser Leu Ala Pro Leu Phe Glu
         3185              3190              3195

GAG CTC CTG CAA CAG TGC CCA CCC GGG GGC CAG AAC AAA ACC ACA CAT    10008
Glu Leu Leu Gln Gln Cys Pro Pro Gly Gly Gln Asn Lys Thr Thr His
3200             3205              3210              3215

ATG GTC TCA GCC TAC CAA CTA GCT CAA GGG AAT TGG GTG CCA GTT AGT    10056
Met Val Ser Ala Tyr Gln Leu Ala Gln Gly Asn Trp Val Pro Val Ser
             3220              3225              3230

TGC CAC GTG TTC ATG GGG ACC ATA CCC GCC AGA AGA ACC AAG ACT CAT    10104
Cys His Val Phe Met Gly Thr Ile Pro Ala Arg Arg Thr Lys Thr His
             3235              3240              3245

CCT TAT GAG GCA TAC GTT AAG CTA AGG GAG TTG GTA GAT GAA CAT AAG    10152
Pro Tyr Glu Ala Tyr Val Lys Leu Arg Glu Leu Val Asp Glu His Lys
         3250              3255              3260

ATG AAG GCA TTA TGT GGC GGA TCA GGC CTA AGT AAG CAC AAC GAA TGG    10200
Met Lys Ala Leu Cys Gly Gly Ser Gly Leu Ser Lys His Asn Glu Trp
         3265              3270              3275

GTA ATT GGC AAG GTC AAG TAT CAA GGA AAC CTG AGG ACC AAA CAC ATG    10248
Val Ile Gly Lys Val Lys Tyr Gln Gly Asn Leu Arg Thr Lys His Met
3280             3285              3290              3295

TTG AAC CCC GGA AAG GTG GCG GAG CAA CTG CAC AGA GAA GGG TAC AGG    10296
Leu Asn Pro Gly Lys Val Ala Glu Gln Leu His Arg Glu Gly Tyr Arg
         3300              3305              3310

CAC AAT GTG TAT AAT AAG ACA ATA GGT TCA GTG ATG ACA GCA ACT GGT    10344
His Asn Val Tyr Asn Lys Thr Ile Gly Ser Val Met Thr Ala Thr Gly
             3315              3320              3325

ATC AGG CTG GAG AAG TTA CCT GTG GTT AGG GCC CAA ACA GAC ACA ACC    10392
Ile Arg Leu Glu Lys Leu Pro Val Val Arg Ala Gln Thr Asp Thr Thr
         3330              3335              3340

AAC TTC CAC CAA GCA ATA AGG GAT AAA ATA GAC AAG GAG GAG AAC CTA    10440
Asn Phe His Gln Ala Ile Arg Asp Lys Ile Asp Lys Glu Glu Asn Leu
         3345              3350              3355

CAG ACC CCT GGC TTG CAT AAG AAG TTA ATG GAA GTC TTC AAT GCA TTA    10488
Gln Thr Pro Gly Leu His Lys Lys Leu Met Glu Val Phe Asn Ala Leu
3360             3365              3370              3375

AAA AGA CCC GAG CTT GAG GCC TCT TAT GAC GCT GTG GAT TGG GAG GAA    10536
Lys Arg Pro Glu Leu Glu Ala Ser Tyr Asp Ala Val Asp Trp Glu Glu
```

-continued

```
                        3380                 3385                  3390
TTG GAG AGA GGA ATA AAT AGG AAG GGT GCT GCT GGT TTC TTC GAA CGC            10584
Leu Glu Arg Gly Ile Asn Arg Lys Gly Ala Ala Gly Phe Phe Glu Arg
            3395                 3400                 3405

AAG AAC ATA GGA GAG GTT TTG GAT TCG GAA AAA AAT AAA GTC GAA GAG            10632
Lys Asn Ile Gly Glu Val Leu Asp Ser Glu Lys Asn Lys Val Glu Glu
            3410                 3415                 3420

GTT ATT GAC AGT TTG AAA AAA GGT AGG AAT ATC AGA TAC TAC GAA ACT            10680
Val Ile Asp Ser Leu Lys Lys Gly Arg Asn Ile Arg Tyr Tyr Glu Thr
            3425                 3430                 3435

GCA ATC CCG AAA AAC GAG AAG AGG GAT GTC AAT GAT GAC TGG ACC GCT            10728
Ala Ile Pro Lys Asn Glu Lys Arg Asp Val Asn Asp Asp Trp Thr Ala
3440                 3445                 3450                 3455

GGT GAC TTC GTA GAT GAG AAG AAG CCA AGA GTG ATA CAA TAC CCT GAG            10776
Gly Asp Phe Val Asp Glu Lys Lys Pro Arg Val Ile Gln Tyr Pro Glu
            3460                 3465                 3470

GCT AAA ACT AGG TTG GCT ATT ACT AAG GTA ATG TAC AAG TGG GTC AAA            10824
Ala Lys Thr Arg Leu Ala Ile Thr Lys Val Met Tyr Lys Trp Val Lys
            3475                 3480                 3485

CAG AAG CCA GTT GTC ATA CCG GGT TAT GAA GGT AAG ACA CCC CTG TTT            10872
Gln Lys Pro Val Val Ile Pro Gly Tyr Glu Gly Lys Thr Pro Leu Phe
            3490                 3495                 3500

CAA ATT TTT GAC AAA GTG AAG AAA GAA TGG GAT CAA TTC CAA AAC CCT            10920
Gln Ile Phe Asp Lys Val Lys Lys Glu Trp Asp Gln Phe Gln Asn Pro
            3505                 3510                 3515

GTG GCA GTT AGC TTT GAT ACC AAA GCG TGG GAT ACC CAG GTA ACC ACA            10968
Val Ala Val Ser Phe Asp Thr Lys Ala Trp Asp Thr Gln Val Thr Thr
3520                 3525                 3530                 3535

AGG GAT TTG GAG CTA ATA AGG GAT ATA CAG AAG TTC TAT TTT AAA AAG            11016
Arg Asp Leu Glu Leu Ile Arg Asp Ile Gln Lys Phe Tyr Phe Lys Lys
            3540                 3545                 3550

AAA TGG CAC AAA TTC ATT GAC ACC CTA ACC AAG CAC ATG TCA GAA GTA            11064
Lys Trp His Lys Phe Ile Asp Thr Leu Thr Lys His Met Ser Glu Val
            3555                 3560                 3565

CCC GTA ATC AGT GCC GAC GGG GAG GTA TAC ATA AGG AAA GGT CAG AGA            11112
Pro Val Ile Ser Ala Asp Gly Glu Val Tyr Ile Arg Lys Gly Gln Arg
            3570                 3575                 3580

GGC AGT GGG CAA CCT GAC ACG AGC GCA GGC AAC AGC ATG TTG AAT GTG            11160
Gly Ser Gly Gln Pro Asp Thr Ser Ala Gly Asn Ser Met Leu Asn Val
            3585                 3590                 3595

TTG ACA ATG GTG TAT GCC TTC TGC GAG GCC ACG GGG GTA CCC TAC AAG            11208
Leu Thr Met Val Tyr Ala Phe Cys Glu Ala Thr Gly Val Pro Tyr Lys
3600                 3605                 3610                 3615

AGT TTT GAC AGA GTG GCA AAG ATC CAT GTC TGC GGG GAT GAT GGT TTC            11256
Ser Phe Asp Arg Val Ala Lys Ile His Val Cys Gly Asp Asp Gly Phe
            3620                 3625                 3630

CTG ATT ACC GAA AGA GCT CTC GGT GAG AAA TTT GCG AGT AAA GGA GTC            11304
Leu Ile Thr Glu Arg Ala Leu Gly Glu Lys Phe Ala Ser Lys Gly Val
            3635                 3640                 3645

CAG ATC CTA TAC GAA GCT GGG AAG CCT CAA AAG ATC ACT GAA GGG GAC            11352
Gln Ile Leu Tyr Glu Ala Gly Lys Pro Gln Lys Ile Thr Glu Gly Asp
            3650                 3655                 3660

AAG ATG AAA GTA GCC TAT CAG TTT GAT GAT ATC GAG TTC TGC TCC CAT            11400
Lys Met Lys Val Ala Tyr Gln Phe Asp Asp Ile Glu Phe Cys Ser His
            3665                 3670                 3675

ACA CCA GTA CAA GTG AGG TGG TCA GAC AAT ACT TCC AGC TAC ATG CCG            11448
Thr Pro Val Gln Val Arg Trp Ser Asp Asn Thr Ser Ser Tyr Met Pro
3680                 3685                 3690                 3695

GGA AGG AAC ACG ACT ACA ATC CTG GCT AAA ATG GCT ACA AGG TTG GAT            11496
Gly Arg Asn Thr Thr Thr Ile Leu Ala Lys Met Ala Thr Arg Leu Asp
```

```
                    3700                    3705                    3710
TCC AGT GGT GAG AGG GGT ACT ATA GCA TAT GAG AAG GCA GTG GCG TTC    11544
Ser Ser Gly Glu Arg Gly Thr Ile Ala Tyr Glu Lys Ala Val Ala Phe
            3715                    3720                    3725

AGC TTT TTG TTG ATG TAC TCC TGG AAC CCA CTG ATC AGA AGG ATA TGC    11592
Ser Phe Leu Leu Met Tyr Ser Trp Asn Pro Leu Ile Arg Arg Ile Cys
            3730                    3735                    3740

TTA CTG GTG TTG TCA ACT GAG TTG CAA GTG AGA CCA GGG AAG TCA ACC    11640
Leu Leu Val Leu Ser Thr Glu Leu Gln Val Arg Pro Gly Lys Ser Thr
            3745                    3750                    3755

ACC TAT TAC TAT GAA GGG GAC CCA ATA TCC GCT TAC AAG GAA GTC ATT    11688
Thr Tyr Tyr Tyr Glu Gly Asp Pro Ile Ser Ala Tyr Lys Glu Val Ile
3760                    3765                    3770                    3775

GGC CAC AAT CTC TTT GAC CTT AAA AGA ACA AGC TTC GAA AAG CTA GCA    11736
Gly His Asn Leu Phe Asp Leu Lys Arg Thr Ser Phe Glu Lys Leu Ala
                3780                    3785                    3790

AAG TTA AAT CTC AGC ATG TCC ACG CTC GGG GTG TGG ACT AGA CAC ACT    11784
Lys Leu Asn Leu Ser Met Ser Thr Leu Gly Val Trp Thr Arg His Thr
            3795                    3800                    3805

AGC AAG AGA TTA CTA CAA GAT TGT GTC AAT GTT GGC ACC AAA GAG GGC    11832
Ser Lys Arg Leu Leu Gln Asp Cys Val Asn Val Gly Thr Lys Glu Gly
            3810                    3815                    3820

AAC TGG CTG GTC AAT GCA GAC AGA CTA GTG AGT AGT AAG ACA GGA AAC    11880
Asn Trp Leu Val Asn Ala Asp Arg Leu Val Ser Ser Lys Thr Gly Asn
            3825                    3830                    3835

AGG TAT ATA CCT GGA GAG GGC CAC ACC CTA CAA GGG AAA CAT TAT GAA    11928
Arg Tyr Ile Pro Gly Glu Gly His Thr Leu Gln Gly Lys His Tyr Glu
3840                    3845                    3850                    3855

GAA CTG ATA CTG GCA AGG AAA CCG ATC GGT AAC TTT GAA GGG ACC GAT    11976
Glu Leu Ile Leu Ala Arg Lys Pro Ile Gly Asn Phe Glu Gly Thr Asp
                3860                    3865                    3870

AGG TAT AAC TTG GGG CCA ATA GTC AAT GTA GTG TTG AGG AGA CTA AAA    12024
Arg Tyr Asn Leu Gly Pro Ile Val Asn Val Val Leu Arg Arg Leu Lys
            3875                    3880                    3885

ATT ATG ATG ATG GCC CTG ATA GGA AGG GGG GTG TGAGCATGGT TGGCCCTTGA   12077
Ile Met Met Met Ala Leu Ile Gly Arg Gly Val
            3890                    3895

TCGGGCCCTA TCAGTAGAAC CCTATTGTAA ATAACATTAA CTTATTAATT ATTTAGATAC   12137

TATTATTTAT TTATTTATTT ATTTATTGAA TGAGCAAGTA CTGGTACAAA CTACCTCATG   12197

TTACCACACT ACACTCATTT TAACAGCACT TTAGCTGGAG GGAAAACCCT GACGTCCACA   12257

GTTGGACTAA GGTAATTTCC TAACGGC                                      12284
```

(2) INFORMATION FOR SEQ ID NO:2:

(i) SEQUENCE CHARACTERISTICS:
        (A) LENGTH: 3898 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
```

```
                 50                      55                      60
Arg Lys Gly Asp Cys Arg Ser Gly Asn His Leu Gly Pro Val Ser Gly
 65                      70                      75                      80

Ile Tyr Ile Lys Pro Gly Pro Val Tyr Tyr Gln Asp Tyr Thr Gly Pro
                         85                      90                      95

Val Tyr His Arg Ala Pro Leu Glu Phe Phe Asp Glu Ala Gln Phe Cys
                100                     105                     110

Glu Val Thr Lys Arg Ile Gly Arg Val Thr Gly Ser Asp Gly Lys Leu
                115                     120                     125

Tyr His Ile Tyr Val Cys Val Asp Gly Cys Ile Leu Leu Lys Leu Ala
                130                     135                     140

Lys Arg Gly Thr Pro Arg Thr Leu Lys Trp Ile Arg Asn Phe Thr Asn
145                     150                     155                     160

Cys Pro Leu Trp Val Thr Ser Cys Ser Asp Asp Gly Ala Ser Gly Ser
                    165                     170                     175

Lys Asp Lys Lys Pro Asp Arg Met Asn Lys Gly Lys Leu Lys Ile Ala
                180                     185                     190

Pro Arg Glu His Glu Lys Asp Ser Lys Thr Lys Pro Pro Asp Ala Thr
                195                     200                     205

Ile Val Val Glu Gly Val Lys Tyr Gln Ile Lys Lys Gly Lys Val
                210                     215                     220

Lys Gly Lys Asn Thr Gln Asp Gly Leu Tyr His Asn Lys Asn Lys Pro
225                     230                     235                     240

Pro Glu Ser Arg Lys Lys Leu Glu Lys Ala Leu Leu Ala Trp Ala Val
                    245                     250                     255

Ile Thr Ile Leu Leu Tyr Gln Pro Val Ala Ala Glu Asn Ile Thr Gln
                260                     265                     270

Trp Asn Leu Ser Asp Asn Gly Thr Asn Gly Ile Gln Arg Ala Met Tyr
                275                     280                     285

Leu Arg Gly Val Asn Arg Ser Leu His Gly Ile Trp Pro Glu Lys Ile
                290                     295                     300

Cys Lys Gly Val Pro Thr His Leu Ala Thr Asp Thr Glu Leu Lys Glu
305                     310                     315                     320

Ile Arg Gly Met Met Asp Ala Ser Glu Arg Thr Asn Tyr Thr Cys Cys
                        325                     330                     335

Arg Leu Gln Arg His Glu Trp Asn Lys His Gly Trp Cys Asn Trp Tyr
                340                     345                     350

Asn Ile Asp Pro Trp Ile Gln Leu Met Asn Arg Thr Gln Thr Asn Leu
                355                     360                     365

Thr Glu Gly Pro Pro Asp Lys Glu Cys Ala Val Thr Cys Arg Tyr Asp
                370                     375                     380

Lys Asn Thr Asp Val Asn Val Thr Gln Ala Arg Asn Arg Pro Thr
385                     390                     395                     400

Thr Leu Thr Gly Cys Lys Lys Gly Lys Asn Phe Ser Phe Ala Gly Thr
                        405                     410                     415

Val Ile Glu Gly Pro Cys Asn Phe Asn Val Ser Val Glu Asp Ile Leu
                420                     425                     430

Tyr Gly Asp His Glu Cys Gly Ser Leu Leu Gln Asp Thr Ala Leu Tyr
                435                     440                     445

Leu Leu Asp Gly Met Thr Asn Thr Ile Glu Asn Ala Arg Gln Gly Ala
                450                     455                     460

Ala Arg Val Thr Ser Trp Leu Gly Arg Gln Leu Ser Thr Ala Gly Lys
465                     470                     475                     480
```

-continued

Lys Leu Glu Arg Arg Ser Lys Thr Trp Phe Gly Ala Tyr Ala Leu Ser
            485                 490                 495

Pro Tyr Cys Asn Val Thr Arg Lys Ile Gly Tyr Ile Trp Tyr Thr Asn
            500                 505                 510

Asn Cys Thr Pro Ala Cys Leu Pro Lys Asn Thr Lys Ile Ile Gly Pro
            515                 520                 525

Gly Lys Phe Asp Thr Asn Ala Glu Asp Gly Lys Ile Leu His Glu Met
            530                 535                 540

Gly Gly His Leu Ser Glu Phe Leu Leu Leu Ser Leu Val Ile Leu Ser
545                 550                 555                 560

Asp Phe Ala Pro Glu Thr Ala Ser Thr Leu Tyr Leu Ile Leu His Tyr
                565                 570                 575

Ala Ile Pro Gln Ser His Glu Glu Pro Glu Gly Cys Asp Thr Asn Gln
            580                 585                 590

Leu Asn Leu Thr Val Lys Leu Arg Thr Glu Asp Val Val Pro Ser Ser
            595                 600                 605

Val Trp Asn Ile Gly Lys Tyr Val Cys Val Arg Pro Asp Trp Trp Pro
            610                 615                 620

Tyr Glu Thr Lys Val Ala Leu Leu Phe Glu Glu Ala Gly Gln Val Ile
625                 630                 635                 640

Lys Leu Val Leu Arg Ala Leu Arg Asp Leu Thr Arg Val Trp Asn Ser
                645                 650                 655

Ala Ser Thr Thr Ala Phe Leu Ile Cys Leu Ile Lys Val Leu Arg Gly
                660                 665                 670

Gln Val Val Gln Gly Ile Ile Trp Leu Leu Leu Val Thr Gly Ala Gln
            675                 680                 685

Gly Arg Leu Ala Cys Lys Glu Asp Tyr Arg Tyr Ala Ile Ser Ser Thr
            690                 695                 700

Asn Glu Ile Gly Leu Leu Gly Ala Glu Gly Leu Thr Thr Thr Trp Lys
705                 710                 715                 720

Glu Tyr Ser His Gly Leu Gln Leu Asp Asp Gly Thr Val Lys Ala Val
                725                 730                 735

Cys Thr Ala Gly Ser Phe Lys Val Thr Ala Leu Asn Val Val Ser Arg
            740                 745                 750

Arg Tyr Leu Ala Ser Leu His Lys Arg Ala Leu Pro Thr Ser Val Thr
            755                 760                 765

Phe Glu Leu Leu Phe Asp Gly Thr Asn Pro Ala Ile Glu Glu Met Asp
770                 775                 780

Asp Asp Phe Gly Phe Gly Leu Cys Pro Phe Asp Thr Ser Pro Val Ile
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Val Glu Cys Thr Ala Val Ser
            820                 825                 830

Pro Thr Thr Leu Arg Thr Glu Val Val Lys Thr Phe Arg Arg Asp Lys
            835                 840                 845

Pro Phe Pro His Arg Val Asp Cys Val Thr Thr Ile Val Glu Lys Glu
            850                 855                 860

Asp Leu Phe His Cys Lys Leu Gly Gly Asn Trp Thr Cys Val Lys Gly
865                 870                 875                 880

Asp Pro Val Thr Tyr Lys Gly Gly Gln Val Lys Gln Cys Arg Trp Cys
                885                 890                 895

Gly Phe Glu Phe Lys Glu Pro Tyr Gly Leu Pro His Tyr Pro Ile Gly
            900                 905                 910

-continued

Lys Cys Ile Leu Thr Asn Glu Thr Gly Tyr Arg Val Val Asp Ser Thr
            915                 920                 925

Asp Cys Asn Arg Asp Gly Val Val Ile Ser Thr Glu Gly Glu His Glu
    930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Glu Gly
                965                 970                 975

Pro Val Arg Lys Thr Ser Cys Thr Phe Asn Tyr Thr Lys Thr Leu Arg
            980                 985                 990

Asn Lys Tyr Tyr Glu Pro Arg Asp Ser Tyr Phe Gln Gln Tyr Met Leu
        995                 1000                1005

Lys Gly Glu Tyr Gln Tyr Trp Phe Asn Leu Asp Val Thr Asp His His
        1010                1015                1020

Thr Asp Tyr Phe Ala Glu Phe Val Leu Val Val Ala Leu Leu
1025                1030                1035                1040

Gly Gly Arg Tyr Val Leu Trp Leu Ile Val Thr Tyr Ile Ile Leu Thr
                1045                1050                1055

Glu Gln Leu Ala Ala Gly Leu Gln Leu Gly Gln Gly Glu Val Val Leu
        1060                1065                1070

Ile Gly Asn Leu Ile Thr His Thr Asp Asn Glu Val Val Val Tyr Phe
        1075                1080                1085

Leu Leu Leu Tyr Leu Val Ile Arg Asp Glu Pro Ile Lys Lys Trp Ile
        1090                1095                1100

Leu Leu Leu Phe His Ala Met Thr Asn Asn Pro Val Lys Thr Ile Thr
1105                1110                1115                1120

Val Ala Leu Leu Met Ile Ser Gly Val Ala Lys Gly Lys Gly Ile Asp
            1125                1130                1135

Gly Gly Trp Gln Arg Gln Pro Val Thr Ser Phe Asp Ile Gln Leu Ala
            1140                1145                1150

Leu Ala Val Val Val Val Val Met Leu Leu Ala Lys Arg Asp Pro
            1155                1160                1165

Thr Thr Phe Pro Leu Val Ile Thr Val Ala Thr Leu Arg Thr Ala Lys
            1170                1175                1180

Ile Thr Asn Gly Phe Ser Thr Asp Leu Val Ile Ala Thr Val Ser Ala
1185                1190                1195                1200

Ala Leu Leu Thr Trp Thr Tyr Ile Ser Asp Tyr Tyr Lys Tyr Lys Thr
            1205                1210                1215

Trp Leu Gln Tyr Leu Val Ser Thr Val Thr Gly Ile Phe Leu Ile Arg
            1220                1225                1230

Val Leu Lys Gly Ile Gly Glu Leu Asp Leu His Ala Pro Thr Leu Pro
            1235                1240                1245

Ser His Arg Pro Leu Phe Tyr Ile Leu Val Tyr Leu Ile Ser Thr Ala
        1250                1255                1260

Val Val Thr Arg Trp Asn Leu Asp Val Ala Gly Leu Leu Leu Gln Cys
1265                1270                1275                1280

Val Pro Thr Leu Leu Met Val Phe Thr Met Trp Ala Asp Ile Leu Thr
            1285                1290                1295

Leu Ile Leu Ile Leu Pro Thr Tyr Glu Leu Thr Lys Leu Tyr Tyr Leu
            1300                1305                1310

Lys Glu Val Lys Ile Gly Ala Glu Arg Gly Trp Leu Trp Lys Thr Asn
            1315                1320                1325

Tyr Lys Arg Val Asn Asp Ile Tyr Glu Val Asp Gln Thr Ser Glu Gly

-continued

```
        1330               1335               1340
Val Tyr Leu Phe Pro Ser Lys Gln Arg Thr Ser Ala Ile Thr Ser Thr
1345               1350               1355               1360

Met Leu Pro Leu Ile Lys Ala Ile Leu Ile Ser Cys Ile Ser Asn Lys
                1365               1370               1375

Trp Gln Leu Ile Tyr Leu Leu Tyr Leu Ile Phe Glu Val Ser Tyr Tyr
                1380               1385               1390

Leu His Lys Lys Val Ile Asp Glu Ile Ala Gly Gly Thr Asn Phe Val
            1395               1400               1405

Ser Arg Leu Val Ala Ala Leu Ile Glu Val Asn Trp Ala Phe Asp Asn
        1410               1415               1420

Glu Glu Val Lys Gly Leu Lys Lys Phe Phe Leu Leu Ser Ser Arg Val
1425               1430               1435               1440

Lys Glu Leu Ile Ile Lys His Lys Val Arg Asn Glu Val Val Arg
                1445               1450               1455

Trp Phe Gly Asp Glu Glu Ile Tyr Gly Met Pro Lys Leu Ile Gly Leu
                1460               1465               1470

Val Lys Ala Ala Thr Leu Ser Arg Asn Lys His Cys Met Leu Cys Thr
            1475               1480               1485

Val Cys Glu Asp Arg Asp Trp Arg Gly Glu Thr Cys Pro Lys Cys Gly
        1490               1495               1500

Arg Phe Gly Pro Pro Val Val Cys Gly Met Thr Leu Ala Asp Phe Glu
1505               1510               1515               1520

Glu Lys His Tyr Lys Arg Ile Phe Ile Arg Glu Asp Gln Ser Gly Gly
                1525               1530               1535

Pro Leu Arg Glu Glu His Ala Gly Tyr Leu Gln Tyr Lys Ala Arg Gly
                1540               1545               1550

Gln Leu Phe Leu Arg Asn Leu Pro Val Leu Ala Thr Lys Val Lys Met
            1555               1560               1565

Leu Leu Val Gly Asn Leu Gly Thr Glu Ile Gly Asp Leu Glu His Leu
        1570               1575               1580

Gly Trp Val Leu Arg Gly Pro Ala Val Cys Lys Lys Val Thr Glu His
1585               1590               1595               1600

Glu Arg Cys Thr Thr Ser Ile Met Asp Lys Leu Thr Ala Phe Phe Gly
                1605               1610               1615

Val Met Pro Arg Gly Thr Thr Pro Arg Ala Pro Val Arg Phe Pro Thr
                1620               1625               1630

Ser Leu Leu Lys Ile Arg Arg Gly Leu Glu Thr Gly Trp Ala Tyr Thr
            1635               1640               1645

His Gln Gly Gly Ile Ser Ser Val Asp His Val Thr Cys Gly Lys Asp
        1650               1655               1660

Leu Leu Val Cys Asp Thr Met Gly Arg Thr Arg Val Val Cys Gln Ser
1665               1670               1675               1680

Asn Asn Lys Met Thr Asp Glu Ser Glu Tyr Gly Val Lys Thr Asp Ser
                1685               1690               1695

Gly Cys Pro Glu Gly Ala Arg Cys Tyr Val Phe Asn Pro Glu Ala Val
                1700               1705               1710

Asn Ile Ser Gly Thr Lys Gly Ala Met Val His Leu Gln Lys Thr Gly
            1715               1720               1725

Gly Glu Phe Thr Cys Val Thr Ala Ser Gly Thr Pro Ala Phe Phe Asp
        1730               1735               1740

Leu Lys Asn Leu Lys Gly Trp Ser Gly Leu Pro Ile Phe Glu Ala Ser
1745               1750               1755               1760
```

-continued

Ser Gly Arg Val Val Gly Arg Val Lys Val Gly Lys Asn Glu Asp Ser
            1765                1770                1775

Lys Pro Thr Lys Leu Met Ser Gly Ile Gln Thr Val Ser Lys Ser Ala
            1780                1785                1790

Thr Asp Leu Thr Glu Met Val Lys Lys Ile Thr Thr Met Asn Arg Gly
            1795                1800                1805

Glu Phe Arg Gln Ile Thr Leu Ala Thr Gly Ala Gly Lys Thr Thr Glu
            1810                1815                1820

Leu Pro Arg Ser Val Ile Glu Glu Ile Gly Arg His Lys Arg Val Leu
1825                1830                1835                1840

Val Leu Ile Pro Leu Arg Ala Ala Ala Glu Ser Val Tyr Gln Tyr Met
            1845                1850                1855

Arg Gln Lys His Pro Ser Ile Ala Phe Asn Leu Arg Ile Gly Glu Met
            1860                1865                1870

Lys Glu Gly Asp Met Ala Thr Gly Ile Thr Tyr Ala Ser Tyr Gly Tyr
            1875                1880                1885

Phe Cys Gln Met Ser Gln Pro Lys Leu Arg Ala Ala Met Val Glu Tyr
            1890                1895                1900

Ser Phe Ile Phe Leu Asp Glu Tyr His Cys Ala Thr Pro Glu Gln Leu
1905                1910                1915                1920

Ala Ile Met Gly Lys Ile His Arg Phe Ser Glu Asn Leu Arg Val Val
            1925                1930                1935

Ala Met Thr Ala Thr Pro Ala Gly Thr Val Thr Thr Thr Gly Gln Lys
            1940                1945                1950

His Pro Ile Glu Glu Phe Ile Ala Pro Glu Val Met Lys Gly Glu Asp
            1955                1960                1965

Leu Gly Ser Glu Tyr Leu Asp Ile Ala Gly Leu Lys Ile Pro Val Glu
            1970                1975                1980

Glu Met Lys Asn Asn Met Leu Val Phe Val Pro Thr Arg Asn Met Ala
1985                1990                1995                2000

Val Glu Ala Ala Lys Lys Leu Lys Ala Lys Gly Tyr Asn Ser Gly Tyr
            2005                2010                2015

Tyr Tyr Ser Gly Glu Asp Pro Ser Asn Leu Arg Val Val Thr Ser Gln
            2020                2025                2030

Ser Pro Tyr Val Val Val Ala Thr Asn Ala Ile Glu Ser Gly Val Thr
            2035                2040                2045

Leu Pro Asp Leu Asp Val Val Val Asp Thr Gly Leu Lys Cys Glu Lys
            2050                2055                2060

Arg Ile Arg Leu Ser Pro Lys Met Pro Phe Ile Val Thr Gly Leu Lys
2065                2070                2075                2080

Arg Met Ala Val Thr Ile Gly Glu Gln Ala Gln Arg Arg Gly Arg Val
            2085                2090                2095

Gly Arg Val Lys Pro Gly Arg Tyr Tyr Arg Ser Gln Glu Thr Pro Val
            2100                2105                2110

Gly Ser Lys Asp Tyr His Tyr Asp Leu Leu Gln Ala Gln Arg Tyr Gly
            2115                2120                2125

Ile Glu Asp Gly Ile Asn Ile Thr Lys Ser Phe Arg Glu Met Asn Tyr
            2130                2135                2140

Asp Trp Ser Leu Tyr Glu Glu Asp Ser Leu Met Ile Thr Gln Leu Glu
2145                2150                2155                2160

Ile Leu Asn Asn Leu Leu Ile Ser Glu Glu Leu Pro Met Ala Val Lys
            2165                2170                2175

Asn Ile Met Ala Arg Thr Asp His Pro Glu Pro Ile Gln Leu Ala Tyr
            2180                2185                2190

```
Asn Ser Tyr Glu Thr Gln Val Pro Val Leu Phe Pro Lys Ile Arg Asn
        2195                2200                2205

Gly Glu Val Thr Asp Thr Tyr Asp Asn Tyr Thr Phe Leu Asn Ala Arg
2210                2215                2220

Lys Leu Gly Asp Asp Val Pro Pro Tyr Val Tyr Ala Thr Glu Asp Glu
2225                2230                2235                2240

Asp Leu Ala Val Glu Leu Leu Gly Leu Asp Trp Pro Asp Pro Gly Asn
        2245                2250                2255

Gln Gly Thr Val Glu Ala Gly Arg Ala Leu Lys Gln Val Val Gly Leu
        2260                2265                2270

Ser Thr Ala Glu Asn Ala Leu Leu Val Ala Leu Phe Gly Tyr Val Gly
        2275                2280                2285

Tyr Gln Ala Leu Ser Lys Arg His Ile Pro Val Val Thr Asp Ile Tyr
        2290                2295                2300

Ser Val Glu Asp His Arg Leu Glu Asp Thr Thr His Leu Gln Tyr Ala
2305                2310                2315                2320

Pro Asn Ala Ile Lys Thr Glu Gly Lys Glu Thr Glu Leu Lys Glu Leu
        2325                2330                2335

Ala Gln Gly Asp Val Gln Arg Cys Val Glu Ala Val Thr Asn Tyr Ala
        2340                2345                2350

Arg Glu Gly Ile Gln Phe Met Lys Ser Gln Ala Leu Lys Val Arg Glu
        2355                2360                2365

Thr Pro Thr Tyr Lys Glu Thr Met Asn Thr Val Ala Asp Tyr Val Lys
        2370                2375                2380

Lys Phe Ile Glu Ala Leu Thr Asp Ser Lys Glu Asp Ile Ile Lys Tyr
2385                2390                2395                2400

Gly Leu Trp Gly Ala His Thr Ala Leu Tyr Lys Ser Ile Gly Ala Arg
        2405                2410                2415

Leu Gly His Glu Thr Ala Phe Ala Thr Leu Val Val Lys Trp Leu Ala
        2420                2425                2430

Phe Gly Gly Glu Ser Ile Ser Asp His Ile Lys Gln Ala Ala Thr Asp
        2435                2440                2445

Leu Val Val Tyr Tyr Ile Ile Asn Arg Pro Gln Phe Pro Gly Asp Thr
        2450                2455                2460

Glu Thr Gln Gln Glu Gly Arg Lys Phe Val Ala Ser Leu Leu Val Ser
2465                2470                2475                2480

Ala Leu Ala Thr Tyr Thr Tyr Lys Ser Trp Asn Tyr Asn Asn Leu Ser
        2485                2490                2495

Lys Ile Val Glu Pro Ala Leu Ala Thr Leu Pro Tyr Ala Ala Lys Ala
        2500                2505                2510

Leu Lys Leu Phe Ala Pro Thr Arg Leu Glu Ser Val Val Ile Leu Ser
        2515                2520                2525

Thr Ala Ile Tyr Lys Thr Tyr Leu Ser Ile Arg Arg Gly Lys Ser Asp
        2530                2535                2540

Gly Leu Leu Gly Thr Gly Val Ser Ala Ala Met Glu Ile Met Ser Gln
2545                2550                2555                2560

Asn Pro Val Ser Val Gly Ile Ala Val Met Leu Gly Val Gly Ala Val
        2565                2570                2575

Ala Ala His Asn Ala Ile Glu Ala Ser Glu Gln Lys Arg Thr Leu Leu
        2580                2585                2590

Met Lys Val Phe Val Lys Asn Phe Leu Asp Gln Ala Ala Thr Asp Glu
        2595                2600                2605

Leu Val Lys Glu Ser Pro Glu Lys Ile Ile Met Ala Leu Phe Glu Ala
```

```
                    2610                2615                2620
Val Gln Thr Val Gly Asn Pro Leu Arg Leu Val Tyr His Leu Tyr Gly
2625                2630                2635                2640

Val Phe Tyr Lys Gly Trp Glu Ala Lys Glu Leu Ala Gln Arg Thr Ala
                    2645                2650                2655

Gly Arg Asn Leu Phe Thr Leu Ile Met Phe Glu Ala Val Glu Leu Leu
                    2660                2665                2670

Gly Val Asp Ser Glu Gly Lys Ile Arg Gln Leu Ser Ser Asn Tyr Ile
        2675                2680                2685

Leu Glu Leu Leu Tyr Lys Phe Arg Asp Asn Ile Lys Ser Ser Val Arg
    2690                2695                2700

Glu Ile Ala Ile Ser Trp Ala Pro Ala Pro Phe Ser Cys Asp Trp Thr
2705                2710                2715                2720

Pro Thr Asp Asp Arg Ile Gly Leu Pro His Asp Asn Tyr Leu Arg Val
                    2725                2730                2735

Glu Thr Lys Cys Pro Cys Gly Tyr Arg Met Lys Ala Val Lys Asn Cys
                    2740                2745                2750

Ala Gly Glu Leu Arg Leu Leu Glu Glu Gly Ser Phe Leu Cys Arg
        2755                2760                2765

Asn Lys Phe Gly Arg Gly Ser Gln Asn Tyr Arg Val Thr Lys Tyr Tyr
2770                2775                2780

Asp Asp Asn Leu Ser Glu Ile Lys Pro Val Ile Arg Met Glu Gly His
2785                2790                2795                2800

Val Glu Leu Tyr Tyr Lys Gly Ala Thr Ile Lys Leu Asp Phe Asn Asn
                    2805                2810                2815

Ser Lys Thr Val Leu Ala Thr Asp Lys Trp Glu Val Asp His Ser Thr
                    2820                2825                2830

Leu Val Arg Ala Leu Lys Arg Tyr Thr Gly Ala Gly Tyr Arg Gly Ala
        2835                2840                2845

Tyr Leu Gly Glu Lys Pro Asn His Lys His Leu Ile Gln Arg Asp Cys
        2850                2855                2860

Ala Thr Ile Thr Lys Asp Lys Val Cys Phe Ile Lys Met Lys Arg Gly
2865                2870                2875                2880

Cys Ala Phe Thr Tyr Asp Leu Ser Leu His Asn Leu Thr Arg Leu Ile
                    2885                2890                2895

Glu Leu Val His Lys Asn Asn Leu Glu Asp Arg Glu Ile Pro Ala Val
                    2900                2905                2910

Thr Val Thr Thr Trp Leu Ala Tyr Thr Phe Val Asn Glu Asp Ile Gly
        2915                2920                2925

Thr Ile Lys Pro Thr Phe Gly Glu Lys Val Thr Pro Glu Lys Gln Glu
        2930                2935                2940

Glu Val Val Leu Gln Pro Ala Val Val Val Asp Thr Thr Asp Val Ala
2945                2950                2955                2960

Val Thr Val Val Gly Glu Thr Ser Thr Met Thr Thr Gly Glu Thr Pro
                    2965                2970                2975

Thr Thr Phe Thr Ser Leu Gly Ser Asp Ser Lys Val Arg Gln Val Leu
                    2980                2985                2990

Lys Leu Gly Val Asp Asp Gly Gln Tyr Pro Gly Pro Asn Gln Gln Arg
        2995                3000                3005

Ala Ser Leu Leu Glu Ala Ile Gln Gly Val Asp Glu Arg Pro Ser Val
        3010                3015                3020

Leu Ile Leu Gly Ser Asp Lys Ala Thr Ser Asn Arg Val Lys Thr Ala
3025                3030                3035                3040
```

-continued

```
Lys Asn Val Lys Ile Tyr Arg Ser Arg Asp Pro Leu Glu Leu Arg Glu
              3045                3050                3055

Met Met Lys Arg Gly Lys Ile Leu Val Val Ala Leu Ser Arg Val Asp
             3060            3065                3070

Thr Ala Leu Leu Lys Phe Val Asp Tyr Lys Gly Thr Phe Leu Thr Arg
         3075            3080            3085

Glu Thr Leu Glu Ala Leu Ser Leu Gly Lys Pro Lys Lys Arg Asp Ile
     3090            3095            3100

Thr Lys Ala Glu Ala Gln Trp Leu Leu Arg Leu Glu Asp Gln Ile Glu
3105            3110            3115            3120

Glu Leu Pro Asp Trp Phe Ala Ala Lys Glu Pro Ile Phe Leu Glu Ala
             3125            3130            3135

Asn Ile Lys Arg Asp Lys Tyr His Leu Val Gly Asp Ile Ala Thr Ile
             3140            3145            3150

Lys Glu Lys Ala Lys Gln Leu Gly Ala Thr Asp Ser Thr Lys Ile Ser
             3155            3160            3165

Lys Glu Val Gly Ala Lys Val Tyr Ser Met Lys Leu Ser Asn Trp Val
             3170            3175            3180

Ile Gln Glu Glu Asn Lys Gln Gly Ser Leu Ala Pro Leu Phe Glu Glu
3185            3190            3195            3200

Leu Leu Gln Gln Cys Pro Pro Gly Gly Gln Asn Lys Thr Thr His Met
             3205            3210            3215

Val Ser Ala Tyr Gln Leu Ala Gln Gly Asn Trp Val Pro Val Ser Cys
             3220            3225            3230

His Val Phe Met Gly Thr Ile Pro Ala Arg Arg Thr Lys Thr His Pro
             3235            3240            3245

Tyr Glu Ala Tyr Val Lys Leu Arg Glu Leu Val Asp Glu His Lys Met
             3250            3255            3260

Lys Ala Leu Cys Gly Gly Ser Gly Leu Ser Lys His Asn Glu Trp Val
3265            3270            3275            3280

Ile Gly Lys Val Lys Tyr Gln Gly Asn Leu Arg Thr Lys His Met Leu
             3285            3290            3295

Asn Pro Gly Lys Val Ala Glu Gln Leu His Arg Glu Gly Tyr Arg His
             3300            3305            3310

Asn Val Tyr Asn Lys Thr Ile Gly Ser Val Met Thr Ala Thr Gly Ile
             3315            3320            3325

Arg Leu Glu Lys Leu Pro Val Val Arg Ala Gln Thr Asp Thr Thr Asn
3330            3335            3340

Phe His Gln Ala Ile Arg Asp Lys Ile Asp Lys Glu Glu Asn Leu Gln
3345            3350            3355            3360

Thr Pro Gly Leu His Lys Lys Leu Met Glu Val Phe Asn Ala Leu Lys
             3365            3370            3375

Arg Pro Glu Leu Glu Ala Ser Tyr Asp Ala Val Asp Trp Glu Glu Leu
             3380            3385            3390

Glu Arg Gly Ile Asn Arg Lys Gly Ala Ala Gly Phe Phe Glu Arg Lys
             3395            3400            3405

Asn Ile Gly Glu Val Leu Asp Ser Glu Lys Asn Lys Val Glu Glu Val
             3410            3415            3420

Ile Asp Ser Leu Lys Lys Gly Arg Asn Ile Arg Tyr Tyr Glu Thr Ala
3425            3430            3435            3440

Ile Pro Lys Asn Glu Lys Arg Asp Val Asn Asp Asp Trp Thr Ala Gly
             3445            3450            3455

Asp Phe Val Asp Glu Lys Lys Pro Arg Val Ile Gln Tyr Pro Glu Ala
             3460            3465            3470
```

```
Lys Thr Arg Leu Ala Ile Thr Lys Val Met Tyr Lys Trp Val Lys Gln
        3475                3480                3485

Lys Pro Val Val Ile Pro Gly Tyr Glu Gly Lys Thr Pro Leu Phe Gln
        3490                3495                3500

Ile Phe Asp Lys Val Lys Lys Glu Trp Asp Gln Phe Gln Asn Pro Val
3505                3510                3515                3520

Ala Val Ser Phe Asp Thr Lys Ala Trp Asp Thr Gln Val Thr Thr Arg
        3525                3530                3535

Asp Leu Glu Leu Ile Arg Asp Ile Gln Lys Phe Tyr Phe Lys Lys Lys
        3540                3545                3550

Trp His Lys Phe Ile Asp Thr Leu Thr Lys His Met Ser Glu Val Pro
        3555                3560                3565

Val Ile Ser Ala Asp Gly Glu Val Tyr Ile Arg Lys Gly Gln Arg Gly
        3570                3575                3580

Ser Gly Gln Pro Asp Thr Ser Ala Gly Asn Ser Met Leu Asn Val Leu
3585                3590                3595                3600

Thr Met Val Tyr Ala Phe Cys Glu Ala Thr Gly Val Pro Tyr Lys Ser
        3605                3610                3615

Phe Asp Arg Val Ala Lys Ile His Val Cys Gly Asp Asp Gly Phe Leu
        3620                3625                3630

Ile Thr Glu Arg Ala Leu Gly Glu Lys Phe Ala Ser Lys Gly Val Gln
        3635                3640                3645

Ile Leu Tyr Glu Ala Gly Lys Pro Gln Lys Ile Thr Glu Gly Asp Lys
        3650                3655                3660

Met Lys Val Ala Tyr Gln Phe Asp Asp Ile Glu Phe Cys Ser His Thr
3665                3670                3675                3680

Pro Val Gln Val Arg Trp Ser Asp Asn Thr Ser Ser Tyr Met Pro Gly
        3685                3690                3695

Arg Asn Thr Thr Thr Ile Leu Ala Lys Met Ala Thr Arg Leu Asp Ser
        3700                3705                3710

Ser Gly Glu Arg Gly Thr Ile Ala Tyr Glu Lys Ala Val Ala Phe Ser
        3715                3720                3725

Phe Leu Leu Met Tyr Ser Trp Asn Pro Leu Ile Arg Arg Ile Cys Leu
        3730                3735                3740

Leu Val Leu Ser Thr Glu Leu Gln Val Arg Pro Gly Lys Ser Thr Thr
3745                3750                3755                3760

Tyr Tyr Tyr Glu Gly Asp Pro Ile Ser Ala Tyr Lys Glu Val Ile Gly
        3765                3770                3775

His Asn Leu Phe Asp Leu Lys Arg Thr Ser Phe Glu Lys Leu Ala Lys
        3780                3785                3790

Leu Asn Leu Ser Met Ser Thr Leu Gly Val Trp Thr Arg His Thr Ser
        3795                3800                3805

Lys Arg Leu Leu Gln Asp Cys Val Asn Val Gly Thr Lys Glu Gly Asn
        3810                3815                3820

Trp Leu Val Asn Ala Asp Arg Leu Val Ser Ser Lys Thr Gly Asn Arg
3825                3830                3835                3840

Tyr Ile Pro Gly Glu Gly His Thr Leu Gln Gly Lys His Tyr Glu Glu
        3845                3850                3855

Leu Ile Leu Ala Arg Lys Pro Ile Gly Asn Phe Glu Gly Thr Asp Arg
        3860                3865                3870

Tyr Asn Leu Gly Pro Ile Val Asn Val Val Leu Arg Arg Leu Lys Ile
        3875                3880                3885

Met Met Met Ala Leu Ile Gly Arg Gly Val
```

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..33
        (D) OTHER INFORMATION: /label= primer_1

(xi) SEQUENCE DESCRIPTION: SEQ ID NO:3:

CCTACTAACC ACGTTAAGTG CTGTGACTTT AAA                      33

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..39
        (D) OTHER INFORMATION: /label= primer_2

(xi) SEQUENCE DESCRIPTION: SEQ ID NO:4:

TTCTGTTCTC AAGGTTGTGG GGCTCACTGC TGTGCACTC                39

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..16
        (D) OTHER INFORMATION: /label= Adaptor_1
            /note= "Upper strand of Bam HI - Hinf I adaptor,
            containing ATG at 364-366"

(xi) SEQUENCE DESCRIPTION: SEQ ID NO:5:

GATCCACCAT GGAGTT                                        16

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..16
        (D) OTHER INFORMATION: /label= Adaptor_2
            /note= "Lower strand of Bam HI - Hinf I adaptor,
            containing ATG at 364-366"

(xi) SEQUENCE DESCRIPTION: SEQ ID NO:6:

GTGGTACCTC AACTTA                                        16

(2) INFORMATION FOR SEQ ID NO:7:

(i) SEQUENCE CHARACTERISTICS:
    (A) LENGTH: 10 base pairs
    (B) TYPE: nucleic acid
    (C) STRANDEDNESS: double
    (D) TOPOLOGY: linear (ix) FEATURE:
    (A) NAME/KEY: -
    (B) LOCATION: 1..10
    (D) OTHER INFORMATION: /label= Adaptor_3
        /note= "Double stranded Stu I - Eco RI blunt adaptor"

(xi) SEQUENCE DESCRIPTION: SEQ ID NO:7:

GCCTGAATTC                                                              10

(2) INFORMATION FOR SEQ ID NO:8:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ix) FEATURE:
    (A) NAME/KEY: -
    (B) LOCATION: 1..21
    (D) OTHER INFORMATION: /label= Adaptor_4
        /note= "Upper strand of Bgl II - BamH I adaptor"

(xi) SEQUENCE DESCRIPTION: SEQ ID NO:8:

GATCCACCAT GGGGGCCCTG T                                                 21

(2) INFORMATION FOR SEQ ID NO:9:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ix) FEATURE:
    (A) NAME/KEY: -
    (B) LOCATION: 1..14
    (D) OTHER INFORMATION: /label= Adaptor_5
        /note= "Lower strand of Bgl II - BamH I adaptor"

(xi) SEQUENCE DESCRIPTION: SEQ ID NO:9:

GTGGTACCCC CGGG                                                         14

(2) INFORMATION FOR SEQ ID NO:10:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ix) FEATURE:
    (A) NAME/KEY: -
    (B) LOCATION: 1..15
    (D) OTHER INFORMATION: /label= Adaptor_6
        /note= "Upper strand of Ban I - Eco R I adaptor"

(xi) SEQUENCE DESCRIPTION: SEQ ID NO:10:

GTGCCTATGC CTGAG                                                        15

(2) INFORMATION FOR SEQ ID NO:11:

(i) SEQUENCE CHARACTERISTICS:
    (A) LENGTH: 15 base pairs
    (B) TYPE: nucleic acid (C) STRANDEDNESS: single
            (D) TOPOLOGY: linear (ix) FEATURE:
            (A) NAME/KEY: -
            (B) LOCATION: 1..15
            (D) OTHER INFORMATION: /label= Adaptor_7
                  /note= "Lower strand of Ban I - Eco R I adaptor"

(xi) SEQUENCE DESCRIPTION: SEQ ID NO:11:

GATACGGACT CTTAA                                                        15

(2) INFORMATION FOR SEQ ID NO:12:

(i) SEQUENCE CHARACTERISTICS:
            (A) LENGTH: 300 base pairs
            (B) TYPE: nucleic acid
            (C) STRANDEDNESS: double
            (D) TOPOLOGY: linear (ii) MOLECULE TYPE: cDNA (vii) IMMEDIATE SOURCE:
            (B) CLONE: lambda gt11 clone (ix) FEATURE:
            (A) NAME/KEY: CDS
            (B) LOCATION: 1..300
            (D) OTHER INFORMATION: /note= "Part of 0.8 kb insert of
                  Lambda gt11"

(xi) SEQUENCE DESCRIPTION: SEQ ID NO:12:

```
AGT GAC AAC GGC ACT AAT GGT ATT CAG CGA GCC ATG TAT CTT AGA GGG         48
Ser Asp Asn Gly Thr Asn Gly Ile Gln Arg Ala Met Tyr Leu Arg Gly
 1               5                  10                  15

GTT AAC AGG AGC TTA CAT GGG ATC TGG CCC GAG AAA ATA TGC AAG GGG         96
Val Asn Arg Ser Leu His Gly Ile Trp Pro Glu Lys Ile Cys Lys Gly
                20                  25                  30

GTC CCC ACT CAT CTG GCC ACT GAC ACG GAA CTG AAA GAG ATA CGC GGG        144
Val Pro Thr His Leu Ala Thr Asp Thr Glu Leu Lys Glu Ile Arg Gly
            35                  40                  45

ATG ATG GAT GCC AGC GAG AGG ACA AAC TAT ACG TGC TGT AGG TTA CAA        192
Met Met Asp Ala Ser Glu Arg Thr Asn Tyr Thr Cys Cys Arg Leu Gln
        50                  55                  60

AGA CAT GAA TGG AAC AAA CAT GGA TGG TGT AAC TGG TAC AAC ATA GAC        240
Arg His Glu Trp Asn Lys His Gly Trp Cys Asn Trp Tyr Asn Ile Asp
 65                  70                  75                  80

CCT TGG ATT CAG TTA ATG AAC AGG ACC CAA ACA AAT TTG ACA GAA GGC        288
Pro Trp Ile Gln Leu Met Asn Arg Thr Gln Thr Asn Leu Thr Glu Gly
                    85                  90                  95

CCT CCA GAT AAG                                                        300
Pro Pro Asp Lys
                100
```

(2) INFORMATION FOR SEQ ID NO:13:

(i) SEQUENCE CHARACTERISTICS:
            (A) LENGTH: 100 amino acids
            (B) TYPE: amino acid
            (D) TOPOLOGY: linear (ii) MOLECULE TYPE: protein (xi) SEQUENCE DESCRIPTION: SEQ ID NO:13:

```
Ser Asp Asn Gly Thr Asn Gly Ile Gln Arg Ala Met Tyr Leu Arg Gly
 1               5                  10                  15

Val Asn Arg Ser Leu His Gly Ile Trp Pro Glu Lys Ile Cys Lys Gly
                20                  25                  30
```

-continued

```
Val Pro Thr His Leu Ala Thr Asp Thr Glu Leu Lys Glu Ile Arg Gly
         35                  40                  45

Met Met Asp Ala Ser Glu Arg Thr Asn Tyr Thr Cys Cys Arg Leu Gln
         50                  55                  60

Arg His Glu Trp Asn Lys His Gly Trp Cys Asn Trp Tyr Asn Ile Asp
 65                  70                  75                  80

Pro Trp Ile Gln Leu Met Asn Arg Thr Gln Thr Asn Leu Thr Glu Gly
             85                  90                  95

Pro Pro Asp Lys
        100
```

HOG CHOLERA VIRUS VACCINE AND DIAGNOSTIC

This is a division of application U.S. Ser. No. 08/873,759 now U.S. Pat. No. 5,811,103, filed Jun. 12, 1997, which is a continuation of U.S. Ser. No. 08/462,495, filed Jun. 5, 1995 now abandoned, which is a divisional of U.S. Ser. No. 08/123,596 now abandoned, filed Sep. 20, 1993, which is a continuation of U.S. Ser. No. 07/797,554 filed Nov. 22, 1991, now abandoned, which is a continuation-in-part of U.S. Ser. No. 07/494,991 now abandoned, filed Mar. 16, 1990.

The present invention is concerned with a nucleic acid sequence, a recombinant nucleic acid molecule comprising such a nucleic acid sequence, a recombinant expression system comprising such a recombinant nucleic acid molecule, a polypeptide characteristic of the hog cholera virus, a vaccine comprising such a polypeptide or recombinant expression system as well as a method for the preparation of such vaccines.

Classical swine fever or hog cholera (HC) represents an economically important disease of swine in many countries worldwide. Under natural conditions, the pig is the only animal known to be susceptible to HC. Hog cholera is a highly contagious disease which causes degeneration in the walls of capillaries, resulting in hemorrhages and necrosis of the internal organs. In the first instance hog cholera is characterized by fever, anorexia, vomiting and diarrhea which can be followed by a chronic course of the disease characterized by infertility, abortion and weak offsprings of sows. However, nearly all pigs die within 2 weeks after the first symptoms appear.

The causative agent, the hog cholera virus (HCV) has been shown to be structurally and serologically related to bovine viral diarrhea virus (BVDV) of cattle and to border disease virus (BDV) of sheep. These viruses are grouped together into the genus pestivirus within the family togaviridae. The nature of the genetic material of pestiviruses has long been known to be RNA, i.e. positive-strand RNA which lacks significant polyadenylation. The HCV probably comprises 3–5 structural proteins of which two are possibly glycosylated. The number of non-structural viral proteins is unknown.

Modified HCV vaccines (comprising attenuated or killed viruses) for combating HC infection have been developed and are presently used. However, infection of tissue culture cells to obtain HCV material to be used in said modified virus vaccines, leads to low virus yields and the virions are hard to purify. Modified live virus vaccines always involve the risk of inoculating animals with partially attenuated pathogenic HCV which is still pathogenic and can cause disease in the inoculated animal or offspring and of contamination by other viruses in the vaccine. In addition the attenuated virus may revert to a virulent state.

There are also several disadvantages using inactivated vaccines, e.g. the risk of only partial inactivation of viruses, the problem that only a low level of immunity is achieved requiring additional immunizations and the problem that antigenic determinants are altered by the inactivation treatment leaving the inactivated virus less immunogenic.

Furthermore, the usage of modified HCV vaccines is not suited for eradication programmes.

Until now, according to our knowledge diagnostic tests in swine which can distinguish between HCV or BVDV infection are not available. This is important as BVDV infection in pigs is of lower significance than HCV infection which means that BVDV infected pigs do not have to be eradicated.

Vaccines containing only the necessary and relevant HCV immunogenic material which is capable of eliciting an immune response against the pathogen do not display above-mentioned disadvantages of modified vaccines.

According to the present invention a nucleic acid sequence encoding a polypeptide characteristic of hog cholera virus has been found. Fragments of said nucleic acid sequence or said polypeptide are also within the present invention. Both the nucleic acid sequence and the polypeptide or fragments thereof can be used for the preparation of a vaccine containing only the necessary and relevant immunogenic material for immunizing animals against HCV infection. "Nucleic acid sequence" refers both to a ribonucleic acid sequence and a deoxy-ribonucleic acid sequence.

A nucleic acid sequence according to the present invention is shown SEQ ID NO: 1. As is well known in the art, the degeneracy of the genetic code permits substitution of bases in a codon resulting in an other codon but still coding for the same amino acid, e.g. the codon for the amino acid glutamic acid is both GAT and GAA. Consequently, it is clear that for the expression of a polypeptide with the amino acid sequence shown in SEQ ID NOS: 1–2 use can be made of a nucleic acid sequence with such an alternative codon composition different from the nucleic acid sequence shown in SEQ ID NO: 1.

Also included within the scope of the invention are nucleic acid sequences which hybridize under stringent conditions to the nucleic acid sequence shown in SEQ ID NO: 1. These nucleic acid sequences are related to the nucleic acid sequence shown in SEQ ID NO: 1 but may comprise nucleotide substitutions, mutations, insertions, deletions etc. and encode polypeptides which are functionally equivalent to the polypeptide shown in SEQ ID NOS: 1–2, i.e. the amino acid sequence of a related polypeptide is not identical with the amino acid sequence shown in SEQ ID NOS: 1–2 but features corresponding immunological properties characteristic for HCV.

Within the scope of the invention are also polypeptides encoded by such related nucleic acid sequences.

The nucleic acid sequence shown in SEQ ID NO: 1 is a cDNA sequence derived from the genomic RNA of HCV. This continuous sequence is 12284 nucleotides in length, and contains one long open reading frame (ORF), starting with the ATG codon at position 364 to 366 and ending with a TGA codon as a translational stop codon at position 12058 to 12060. This ORF consists of 3898 codons capable of encoding 435 kDa of protein.

In vivo, during HCV replication in an infected cell, this protein is synthesized as a polyprotein precursor molecule which is subsequently processed to fragment polypeptides by (enzymatic) cleavage of the precursor molecule. These fragments form after possible post-translational modifications the structural and non-structural proteins of the virus. A preferred nucleic acid sequence contains the genetic information for such a fragment with immunizing properties against HCV or immunological properties characteristic for HCV or contains the genetic information for a portion of such a fragment which still has the immunizing properties or the immunological properties characteristic for HCV.

The term "fragment or portion" as used herein means a DNA or amino acid sequence comprising a subsequence of one of the nucleic acid sequences or polypeptides of the invention. Said fragment or portion is or encodes a polypeptide having one or more immunoreactive and/or antigenic determinants of a HCV polypeptide, i.e. has one or more epitopes which are capable of eliciting an immune response in pigs and/or is capable of specifically binding to a complementary antibody. Such epitope containing sequences are at least 5–8 residues long (Geysen, H. M. et al., 1987). Methods for determining usable polypeptide fragments are outlined below. Fragments or portions can inter alia be produced by enzymatic cleavage of precursor molecules, using restriction endonucleases for the DNA and proteases for the polypeptides. Other methods include chemical synthesis of the fragments or the expression of polypeptide fragments by DNA fragments.

Fragment polypeptides of the polypeptide according to SEQ ID NOS: 1–2 and the portions thereof, which can be used for the immunisation of animals against HC or for diagnosis of HC also form part of the present invention. A fragment-coding region is located within the amino acid position about 1–249, 263–487, 488–688 or 689–1067. The 1–249 region essentially represents the core protein whereas the 263–487, 488–688 and 689–1067 regions essentially represent glycoproteins of 44/48 kD, 33 kD and 55 kD respectively. Within the scope of the invention are also nucleic acid sequences comprising the genetic information for one or more of the coding regions mentioned above or portions thereof.

A preferred region to be incorporated into a vaccine against HCV infection is the region corresponding to the 55 kD protein of HCV or a portion thereof still having immunizing activity.

Furthermore, a nucleic acid sequence at least comprising the coding sequences for said 55 kD protein or portion thereof can advantageously be applied according to the present invention.

In addition, a preferred portion of the HCV 55 kD protein, which can be used for immunization of pigs against HCV infection, is determined by analyses of HCV deletion mutants with anti-55 kD protein monoclonal antibodies having virus neutralizing activity. Such a portion comprising an epitope spans the amino acid sequence about 812–859 and is coded by the nucleotide sequence about 2799–2938. A polypeptide at least comprising said amino acid sequence or a nucleic acid sequence at least comprising said nucleotide sequence form part of the present invention too.

A nucleic acid sequence according to the invention which can be used for the diagnosis of HCV infection in pigs and which can be applied to discriminate HCV from BVDV can be derived from the gene encoding the 55 kD protein.

Preferably, such a nucleic acid sequence is derived from the nucleotide sequences 2587–2619 or 2842–2880, both sequences being part of the gene encoding the 55 kD protein. A preferred oligonucleotide for diagnostic purposes is (SEQ ID NOS: 3 and 4, respectively):
5'-CCT ACT AAC CAC GTT AAG TGC TGT GAC TTT AAA-3'
or
5'-TTC TGT TCT CAA GGT TGT GGG GCT CAC TGC TGT GCA CTC-3'

Moreover, a nucleic acid sequence comprising at least a sub-sequence of said oligonucleotides and which still can be used to differentiate between HCV and BVDV forms part of the invention.

The invention also relates to a test kit to be used in an assay, this test kit containing a nucleic acid sequence according to the invention.

Preferably the test kit comprises an oligonucleotide mentioned above or a nucleic acid sequence comprising at least a sub-sequence thereof.

Variations or modifications in the polypeptide shown in SEQ ID NOS: 1–2 or fragments thereof, such as natural variations between different strains or other derivatives, are possible while retaining the same immunologic properties. These variations may be demonstrated by (an) amino acid difference(s) in the overall sequence or by deletions, substitutions, insertions, inversions or additions of (an) amino acid(s) in said polypeptide.

Moreover, the potential exists, in the use of recombinant DNA technology, for the preparation of various derivatives of the polypeptide shown in SEQ ID NOS: 1–2 or fragments thereof, variously modified by resultant single or multiple amino acid substitutions, deletions, additions or replacements, for example by means of site directed mutagenesis of the underlying DNA. All such modifications resulting in derivatives of the polypeptide shown in SEQ ID NOS: 1–2 or fragments thereof are included within the scope of the present invention so long as the essential characteristic activity of said polypeptide or fragment thereof, remains unaffected in essence.

RNA isolated from pelleted virions was isolated and used for the synthesis of cDNA. This cDNA was cloned in phage λgt11 and the respective library was amplified and screened with goat anti-HCV antiserum. Two positive clones could be identified and shown to have inserts with sizes of 0.8 kb and 1.8 kb. The 0.8 kb λgt11 insert was partially sequenced (see SEQ ID NOS: 12–13)) and determined to be located between about 1.2 and 2.0 kb on the HCV genome (see SEQ ID NO: 1).

A nucleic acid sequence according to the invention which can be used for the diagnosis of HCV in infected animals and which surprisingly can be applied to discriminate HCV from BVDV is represented by the nucleotide sequence 5551–5793 shown in SEQ ID NO: 1.

Moreover, a nucleic acid sequence comprising at least a sub-sequence of said nucleotide sequence and which still can be used to differentiate between HCV and BVDV forms part of the invention.

The invention also relates to a test kit to be used in an assay, this test kit containing a nucleic acid sequence according to the invention.

Preferably the test kit comprises the nucleic acid sequence represented by the nucleotide sequence 5551–5793 shown in SEQ ID NO: 1 or a nucleic acid sequence comprising at least a subsequence thereof mentioned above.

RNA isolated from pelleted virions was isolated and used for the synthesis of cDNA. This cDNA was cloned in phage λgt11 and the respective library was amplified and screened with goat anti-HCV antiserum. Two positive clones could be identified and shown to have inserts with sizes of 0.8 kb and 1.8 kb. The 0.8 kb λgt11 insert was partially sequenced (see SEQ ID NOS: 12–13) and determined to be located between about 1.2 and 2.0 kb on the HCV genome (see SEQ ID NO: 1).

A nucleic acid sequence according to the present invention can be ligated to various vector nucleic acid molecules such as plasmid DNA, bacteriophage DNA or viral DNA to form a recombinant nucleic acid molecule. The vector nucleic acid molecules preferably contain DNA sequences to initiate, control and terminate transcription and translation. A recombinant expression system comprising a host containing such a recombinant nucleic acid molecule can be used to allow for a nucleic acid sequence according to the present invention to express a polypeptide encoded by said nucleic acid sequence. The host of above-mentioned recombinant expression system can be of procaryotic origin, e.g. bacteria such as *E.coli, B.subtilis* and Pseudomonas, viruses such as vaccinia and fowl pox virus or eucaryotic origin such as yeasts or higher eucaryotic cells such as insect, plant or animal cells.

Immunization of animals against HC can, for example, be achieved by administering to the animal a polypeptide according to the invention as a so-called "sub-unit" vaccine. The subunit vaccine according to the invention comprises a polypeptide generally in a pure form, optionally in the presence of a pharmaceutically acceptable carrier.

Small fragments are preferably conjugated to carrier molecules in order to raise their immunogenicity. Suitable carriers for this purpose are macromolecules, such as natural polymers (proteins, like key hole limpet hemocyanin, albumin, toxins), synthetic polymers like polyamino acids (polylysine, polyalanine), or micelles of amphiphilic compounds like saponins. Alternatively these fragments may be provided as polymers thereof, preferably linear polymers. Polypeptides to be used in such subunit vaccines can be prepared by methods known in the art, e.g. by isolation said polypeptides from hog cholera virus, by recombinant DNA techniques or by chemical synthesis.

If required the polypeptides according to the invention to be used in a vaccine can be modified in vitro or in vivo, for example by glycosylation, amidation, carboxylation or phosphorylation.

An alternative to subunit vaccines are "vector" vaccines. A nucleic acid sequence according to the invention is integrated by recombinant techniques into the genetic material of another micro-organism (e.g. virus or bacterium) thereby enabling the micro-organism to express a polypeptide according to the invention. This recombinant expression system is administered to the animal to be immunized whereafter it replicates in the inoculated animal and expresses the polypeptide resulting in the stimulation of the immune system of the animal. Suitable examples of vaccine vectors are pox viruses (such as vaccinia, cow pox, rabbit pox), avian pox viruses (such as fowl pox virus) pseudorabies virus, adeno viruses, influenza viruses, bacteriophages or bacteria (such as *Escherichia coli* and Salmonella).

The recombinant expression system having a nucleic acid sequence according to the invention inserted in its nucleic acid sequence can for example be grown in a cell culture and can if desired be harvested from the infected cells and formed to a vaccine optionally in a lyophilized form. Said genetically manipulated micro-organism can also be harvested from live animals infected with said micro-organism. Abovementioned recombinant expression system can also be propagated in a cell culture expressing a polypeptide according to the invention, whereafter the polypeptide is isolated from the culture.

A vaccine comprising a polypeptide or a recombinant expression system according to the present invention can be prepared by procedures well-known in the art for such vaccines. A vaccine according to the invention can consist inter alia of whole host, host extract, partially or completely purified polypeptide or a partially or completely purified recombinant expression system as above-mentioned.

The vaccine according to the invention can be administered in a conventional active immunization scheme: single or repeated administration in a manner compatible with the dosage formulation and in such amount as will be therapeutically effective and immunogenic. The administration of the vaccine can be done, e.g. intradermally, subcutaneously, intramusculary, intra-venously or intranasally. For parenteral administration the vaccines may additionally contain a suitable carrier, e.g. water, saline or buffer solution with or without adjuvants, stabilizers, solubilizers, emulsifiers etc.

The vaccine may additionally contain immunogens related to other diseases or nucleic acid sequences encoding these immunogens like antigens of parvovirus, pseudorabies virus, swine influenza virus, TGE virus, rotavirus, *Escherichia coli*, Bordetella, Pasteurella, Erysipelas etc. to produce a multivalent vaccine.

Polypeptides according to the present invention can also be used in diagnostic methods to detect the presence of HCV antigen or antibody in an animal. Moreover, nucleic acid sequences according to the invention can be used to produce polypeptides to be used in above-mentioned diagnostic methods or as a hybridisation probe for the detection of the presence of HCV nucleic acid in a sample.

EXAMPLE 1

Immunological Identification of cDNA Clones

Infection of cells and harvesting of virus. PK15 and $38A_1D$ cells were grown in DMEM with 10% FCS and were infected in suspension by the virulent HCV strain Alfort in a volume of 20–30 ml at a cell concentration of $5\times10^7$/ml at 37° C. for 90 min with an m.o.i. of 0.01 to 0.001 (as determined by immunofluorescence assay). Thereafter, the PK15 cells were seeded in tissue culture plates (150 mm diameter), while the suspension cells $38A_1D$ were incubated in bottles with gentle stirring (Tecnomara, Switzerland). For cDNA synthese, the tissue culture supernatant was harvested 48 hours after infection, clarified at 12,000 g, and afterwards the virus pelleted in a TFA 20 rotor (Contron, Italy) at 54,000 g for 12 hours.

Preparation of goat anti-HCV serum. A fibroblastic cell strain was established from the skin biopsy of a young goat by standard cell culture techniques. The cells were initially grown in F-10 medium with 10% FCS and later in DMEM with 10% FCS. Goat fibroblasts were infected with HCV. Over the first 26 hours p.i., the cells were washed every 8 hours 3 times with PBS and afterwards incubated in DMEM with 10% preimmune goat serum (PGS). 48 hours p.i., the tissue culture supernatant was harvested and used as stock virus. Before immunization, goat cells for 30 tissue culture dishes (150 mm diameter) were kept for 3 passages in medium with 10% PGS and then infected with the stock virus. 48 hours p.i., the goat was immunized with X-ray-inactivated pelleted virus and infected cells. Both were emulsified in Freund's adjuvant (complete for basis immunization, incomplete for booster injections) and injected subcutaneously. To obtain antibodies recognizing denatured molecules, the antigen preparations were incubated in 0.2% SDS, 3 mM DTT at 95° C. for 5 min before injection.

RNA Preparation, cDNA synthesis and cloning. RNA from virions was isolated by using the guanidine thiocyanate method described by Chirgwin et al. (1979). RNA from pelleted virions (5 μg total RNA, approximately 0.5 μg HCV RNA) and 0.1 μg of random hexanucleotide primer (Pharmacia, Sweden) in 20 μl of water were heated to 65° C. for 10 min, chilled on ice, and adjusted to first strand buffer (50 mM Tris-HCl pH 8.3; 30 mM KCl; 8 mM $MgCl_2$; 1 mM DTT, dATP, dCTP, dGTP, dTTP 1 mM each and 500 units RNAguard [Pharmacia, Sweden] per ml) in a final volume of 32 μl. 35 units of AMV reverse transcriptase (Life Sciences Inc., USA) were added. After 1 hour at 43° C. the reaction mixture was added to one vial of second strand synthesis mixture (cDNA synthesis kit, Pharmacia, Sweden). Second strand synthesis, preparation of blunt ends, and Eco RI adaptor ligation and phosphorylation were done as recommended by the supplier.

The cDNA was size-fractionated by preparative agarose gel electrophoresis. The part of the gel containing DNA molecules smaller than 0.5 kb was discarded. The remaining DNA was concentrated by running the gel reversely for 15 min and extracted from the agarose after 3 cycles of freezing and thawing with phenol.

Ethanol co-precipitated cDNA and λgt11 DNA (1 μg EcoRI digested dephosphorylated arms, Promega, USA) was ligated by 3 units of T4 DNA ligase (Pharmacia, Sweden) in a total volume of 10 μl ligase buffer (30 mM Tris-HCl pH 7.4; 10 mM MgCl$_2$; 10 mM DTT; 1 mM ATP). In vitro packaging with a commercially available extract (Packagene, Promega, USA) and infection of E.coli K12 cells, strain Y 1090, with resulting phages was performed as recommended by the supplier. The library was amplified once as described (Davis et al., 1986).

Screening of λgt11 library. Screening was basically performed as described (Young and Davis, 1983) using the Protoblot system purchased from Promega, USA (Huynh et al., 1985) and a serum dilution 10$^{-3}$. For background reduction the goat anti HCV serum was treated with E.coli lysate (strain Y1090) at 0.8 mg/ml (Huynh et al., 1985). Two positive clones having inserts of 0.8 kb and 1.8 kb, respectively could be identified.

Nick translation and Northern hybridization. 50 ng of the 0.8 kb HCV nucleic acid sequence labeled with [α$^{32}$P]dCTP (3000 Ci per mMole, Amersham Buchler, FRG) by nick translation (nick translation kit, Amersham Buchler, FRG) was hybridized to Northern filters at a concentration of 5 ng per ml of hybridization mixture (5× SSC; 1× Denhardt's; 20 mM sodium phosphate pH 6.8; 0.1% SDS and 100 μg yeast tRNA [Boehringer-Mannheim, FRG] per ml) at 68° C. for 12 to 14 hours. Membranes were then washed as described (Keil et al., 1984) and exposed at −70° C. to Kodak X-Omat AR films for varying times using Agfa Curix MR 800 intensifying screens.

The 0.8 kb nucleic acid sequence hybridized not only to intact HCV RNA but also to degradation products thereof. The 0.8 kb nucleic acid sequence did not hybridize to the 1.8 kb nucleic acid sequence, indicating that these two nucleic acid sequences correspond with fragments of the HCV genome which are not located in the same region of the genomic RNA.

Nucleotide sequencing. Subcloning of HCV specific phage DNA inserts into plasmid pEMBL 18 plus was done according to standard procedures (Maniatis et al., 1982). Single-stranded DNA of recombinant pEMBL plasmids was prepared as described (Dente et al., 1985). Dideoxy sequencing reactions (Sanger et al., 1977) were carried out as recommended by the supplier (Pharmacia, Sweden).

EXAMPLE 2

Molecular Cloning and Nucleotide Sequence of the Genome of HCV

RNA preparation, cDNA synthesis and cloning. RNA preparation, cDNA synthesis, size selection and ligation of co-precipitated cDNA and λgt10 DNA (1 μg EcoRI digested dephosphorylated arms, Promega, USA) were done as described above. In vitro packaging of phage DNA using Packagene (Promega, USA) and titration of phages on E.coli strain C 600 HFL were performed as suggested by the supplier. The library was amplified once (Davis et al., 1986), and replicas transferred to nictrocellulose membranes (Amersham Buchler, FRG) (Benton and Davis, 1977) were hybridized with oligonucleotides as described above for Northern hybridization. Screening with cDNA fragments labeled with [α$^{32}$P] dCTP by nick translation (nick translation kit, Amersham Buchler, FRG) was done as described by Benton and Davis (1977). Positive clones were plaque purified and inserts subcloned into pEMBL plasmids (Maniatis et al., 1982; Dente et al., 1985; Davis et al., 1986).

A $^{32}$P 5'-end labeled oligonucleotide of 17 bases complementary to the RNA sequence encoding the amino acid sequence Cys Gly Asp Asp Gly Phe was used for screening a λgt10 cDNA library. This oligonucleotide which hybridized to the about 12 kb genomic RNA of HCV, identified inter alia a clone with an insert of 0.75 kb, which hybridized also to HCV RNA. This 0.75 kb nucleic acid sequence which represents a fragment of the HCV genome together with the 0.8 kb λgt11 nucleic acid sequence insert were used for further library screening resulting in a set of overlapping HCV nucleic acid sequences of which the relative positions and restriction site maps are shown in FIG. 1. These nucleic acid sequence fragments of the HCV genome are located between the following nucleic acid positions 4.0 kb fragment: 27–4027
4.5 kb fragment: 54–4494
0.8 kb fragment: 1140–2002
4.2 kb fragment: 3246–7252
5.5 kb fragment: 6656–11819 and within about the following nucleic acid positions 3.0 kb fragment: 8920–11920
1.9 kb fragment: 10384–12284
0.75 kb fragment: 10913–11663

Nucleotide sequencing. For complete nucleotide sequence determination exonuclease III and nuclease S1 (enzymes from Boehringer Mannheim, FRG) were used to establish deletion libraries of HCV derived cDNA inserts subcloned into pEMBL 18+ or 19+ plasmids (Hennikoff, 1987). Dideoxy sequencing (Sanger et al. 1977) of single stranded (Dente et al., 1985) or double stranded DNA templates was carried out using the T7 polymerase sequencing kit (Pharmacia, Sweden).

From the cDNA fragments a continuous sequence of 12284 nucleotides in length could be determined as shown in SEQ ID NO: 1. This sequence contains one long open reading frame (ORF), starting with the ATG codon at position 364 to 366 and ending with TGA as a translational stop codon at 12058 to 12060. This ORF consists of 3898 codons capable of encoding a 435 kDa protein with an amino acid sequence shown in SEQ ID NOS: 1–2. Three nucleotide exchanges were detected as a result of differences in nucleotide sequence caused by possible heterogenicity of the virus population, two of which resulted in changes in the deduced amino acid sequence (SEQ ID NOS: 1–2).

It is concluded that almost the complete HCV genome has been cloned and sequenced by the procedures described above.

The 0.8 kb λgt11 nucleic acid sequence encoding an immunogenic HCV polypeptide identified with anti HCV serum was partially sequenced (SEQ ID NOS: 12–13) which revealed that this sequence is located within 1.2 and 2.0 kb on the HCV RNA.

EXAMPLE 3

Molecular Cloning and Expression of Fusion Proteins of HCV cDNA fragments derived from two regions of the HCV genome, i.e. the 0,8 kb λgt11 insert of example 1 encoding amino acids 262–546 (see SEQ ID NOS: 1–2) and the nucleic acid sequence encoding amino acids 747–1071

(SEQ ID NOS: 1–2), are expressed as fusion proteins in the pEx system (Strebel, K. et al., 1986).

Bacterial extracts were separated by SDS-PAGE and stained according to standard procedures, and then tested for reactivity with the goat anti-HCV serum of example 1 in a Western blot.

The HCV specific fusion proteins were partially purified by SDS-PAGE and transfered to nitrocellulose and incubated with the goat anti-HCV serum. Specific antibodies against said fusion proteins were obtained after elution.

Antibodies specific for the above-mentioned fusion proteins were employed in a radio-immuno precipitation assay.
Results Both fusion proteins expressed in the pEx system were clearly identified as HCV specific after reaction with the goat anti-HCV serum.

Monospecific antiserum prepared against both fusions proteins precipitated HCV glycoproteins.

Antibodies specific for the 262–546-fusion protein precipitated the 44/48 kD and 33 kD protein, antibodies specific for the 747–1071-fusion protein precipitated the 55 kD protein from virus infected cells.

EXAMPLE 4

Molecular Cloning and Expression of Structural Proteins Via Vaccinia Virus

A fragment of the 4.0 kb clone shown in FIG. 1 (pHCK11) is prepared starting at the HinfI restriction site (nucleotide 372) and ending at an artificial EcoRI site (nucleotide 4000) (Maniatis et al. 1982). For the 5' end an oligonucleotide adaptor was synthesized which contained an overhang compatible to BamHI, the original ATG(364–366) as translational start codon and a protruding end compatible to HinfI at the 3' end (SEQ ID NOS: 5 and 6).

```
5'  GATCCACCATGGAGTT       HinfI
    BamHI   GTGGTACCTCAACTTA  5'
```

At the 3' end of the construct a translational stop codon was introduced by deletion of the EcoRI protruding end with Mung bean nuclease and ligation into a blunt-end StuI/EcoRI adaptor residue (SEQ ID NO: 7):

```
5'  GCCTGAATTC   3'EcoRI
    CGGACTTAAG
```

(Maniatis et al. 1982).

Prior to inserting above-mentioned HCV sequences into vaccinia virus the heterologous gene is cloned into a recombination vector. For this purpose a pGS62 plasmid (Cranage, M. P. et al. 1986) was used which contains a cloning site downstream the P7.5K promotor within the 4.9 kb thymidine kinase sequence. The cloning site comprises three unique restriction sites, BamHI, SmaI and EcoRI. The recombination vector pGS62-3.8 was established by ligation of the described HCV sequence (372–4000) together with the adaptors into the BamHI/EcoRI digested pGS62.

Based on the plasmid a set of 15 deletion mutants was established. By treatment with ExonucleaseIII (Hennikof et al., 1987) subsequent shortening of the HCV cDNA from the 3' end was performed. All deletions are located within the region coding for the HCV 55 kD protein by removal of about 100 bp; most of the 55 kD protein is lost in mutant 15 ending at nucleotide 2589. ExoIII shortened cDNA clones were ligated into the pGS62 giving rise to pGS62-3.8Exo 1–15 (FIG. 2).

CVI cells were infected with vaccinia (strain Copenhagen, mutant TS7) at a MOI of 0.1. Three hours after infection pGS62-3.8 DNA as well as vaccinia WR DNA were transfected by the $Ca_3(PO_4)_2$ precipitation method and incubated for two days. Virus progeny was harvested and selected for tk-phenotype on 143 tk-cells in the presence of brom-deoxy-Uridine (100 μg/ml). This selection was performed at least twice followed by two further cycles of plaque purification.

Characterization of Vaccinia-HCV Recombinants

CVI cells were infected at an MOI between 2 and 10 with vaccinia-HCV recombinants and incubated for 8–16 hours. After fixation of the cells indirect immunofluorescence was performed using either monoclonal antibodies specific for HCV 55 kD protein or polyvalent anti-HCV sera. In all cases a cytoplasmatic fluorescence could be demonstrated.

After radioimmunoprecipitation and western blot analysis of cells infected with vaccinia recombinants four HCV-specific proteins were detected. By labeling with [$^3$H] glucosamine it was shown that three of these proteins are glycosylated. The apparent molecular weights of these proteins were identical to those found in HCV infected cells with HCV specific sera, namely 20 kD(core), 44/48 kD, 33 kD and 55 kD.

Proteolytic processing and modifications appear to be authentic since HCV proteins produced by expression via vaccinia virus have the same apparent molecular weights as in HCV-infected cells.

Induction of Neutralizing Antibodies Against HCV in Mice

Four groups of mice (3 mice/group) were infected once with

| | | |
|---|---|---|
| a. Vaccinia WR wildtype | ($5 \times 10^6$pfu/individual) | WR |
| b. Vaccinia 3.8 recombinant | ($5 \times 10^7$pfu/individual) | VAC3.8 |
| c. Vaccinia 3.8Exo 4 (55 kD deleted) | ($5 \times 10^7$pfu/individual) | VAC3.8Exo 4 |
| d. Vaccinia 3.8Exo 5 | ($5 \times 10^7$pfu/individual) | VAC3.8Exo 5 |
| e. Vaccinia 3.8Exo 15 (55 kD deleted) | ($5 \times 10^7$pfu/individual) | VAC3.8Exo 15 | by injection of purified virus intraperitoneally. Mice were bled three weeks later. The reactivity of the sera was checked in a virus neutralization assay with HCV (Alfort) on PK[15] cells after serial dilution. (Rümenapf, T. et al. 1989).

| Neutralization titers | |
|---|---|
| a. WR | <1:2 |
| b. VAC3.8 | 1:96 |
| c. VAC3.8Exo 4 | 1:96 |
| d. VAC3.8Exo 5 | <1:2 |
| e. VAC3.8Exo 15 | <1.2 |

From the above it can be concluded that vaccinia virus containing a nucleic acid sequence comprising the genetic information for all structural proteins (VAC3.8) is able to induce virus neutralizing antibodies in mice, while incomplete constructs VAC3.8Exo 5–15 and WR are not.

As all deletions are located within the region coding for HCV 55 kD protein (most of the 55 kD protein is lost in mutant 15 ending at nucleotide 2589) and the other structural proteins are still being expressed by the recombinant vaccinia virus, it is clear that the 55 kD protein is responsible for the induction of HCV neutralizing antibodies.

EXAMPLE 5

Immunization of Pigs With VAC3.8

Out of three piglets (about 20 kg in weight) one animal (no. 28) was infected with wild type vaccinia virus (WR strain) and the other two (nos. 26, 27) with recombinant VAC3.8 (i.p., i.v. and i.d., respectively). For infection $1 \times 10^8$ pfu of vaccinia virus is applied to each animal.

Clinical signs in the course of vaccinia infection were apparent as erythema at the side of scarification and fever (41° C.) at day six after infection.

Titers Against Vaccinia and Hog Cholera Virus:

Three weeks after infection the reactivity of the respective sera against vaccinia (WR on CVI cells) and HCV (Alfort on PK15 cells) was checked.

Neutralization was assayed after serial dilution of the sera by checking for complete absence of cpe (vaccinia) or specific signals in immunofluorescence (HCV). (Rümenapf, T. et al. 1989).

| Neutralization titers against vaccinia: | |
|---|---|
| pig 28 (WR) | 1:8 |
| pig 26 (VAC3.8) | 1:16 |
| pig 27 (VAC3.8) | 1:16 |
| Neutralization titers against HCV: | |
| pig 28 (WR) | <1:2 |
| pig 26 (VAC3.8) | 1:32 |
| pig 27 (VAC3.8) | 1:16 |

Challenge with HCV:

Four weeks after immunization with vaccinia each of the pigs was challenged by infection with $5 \times 10^7$ TCID$_{50}$ HCV Alfort. Virus was applicated oronasal according to the natural route of infection. This amount of virus has been experimentally determined to be compulsory lethal for pigs.

On day five after the challenge infection pig 28 revealed fever of 41.5° C. and kept this temperature until day 12. The moribund animal was killed that day expressing typical clinical signs of acute hog cholera.

Both pigs (26, 27) immunized with VAC3.8 did not show any sign of illness after the challenge with HCV for more than 14 days.

EXAMPLE 6

Construction of a 55 kD Protein Expression Vector

A. PRV Vector.

Clone pHCK11 is digested with restriction enzymes SacI and HpaI according to standard techniques.

The resulting 1.3 kb fragment, located between nucleotides 2672 (AGCTC) and 3971 (GTT) comprising most of HCV 55 kD protein, is isolated and cloned into the pseudorabies virus (PRV) gX gene (Maniatis et al. 1982).

Briefly, the cloned gX sequence was digested with SacI and ApaI. The ApaI 5' protruding ends were made blunt by filling up with Klenow fragment. After ligation the putative gX leader peptide coding sequence was located just upstream of the inserted HCV 55 kD sequence.

A translational stop codon downstream the HCV sequence was introduced by digestion with Bgl II (Bgl II site: 3936–3941) and religation after filling up the overhangs with Klenow fragment. This construct was placed downstream of the PRV gX promotor (clone 16/4-1.3). Clone 16/4-1.3 was transfected into MDBK cells by the DEAE dextran method (Maniatis et al. 1989). 16 h. later cells were infected with PRV (m.o.i.=i). 4 h. post infection cells were fixed with a mixture of cold (−20° C.) methanol/acetone. Indirect immunofluorescence with monoclonal antibodies (MABs) anti-HCV 55 kD protein revealed a specific signal in 5–10% of the cells. PRV infected cells without transfection and cells only transfected with clone 16/4-1.3 did not show any signal in this assay.

B. Vaccinia Vector.

Clone pHCK11 is digested with restriction enzymes NheI and HpaI according to standard techniques. NheI 5' protruding end was made blunt by treatment with mung bean nuclease. The resulting 1.5 kb fragment, located between nucleotides 2438 (C) and 3971 (GTT) comprising HCV 55 kD protein, is isolated and cloned into the pseudorabies virus (PRV) gx gene (Maniatis et al., 1989).

The cloned gx sequence was digested with SacI and ApaI. SacI and ApaI 3' protruding ends were made blunt by exonuclease treatment with Klenow fragment. After ligation the putative gx leader peptide coding sequence was located upstream of the inserted HCV 55 kD sequence.

A translational stop codon downstream the HCV sequence was introduced by digestion with BglII (BglII site 3936–3941) and religation after filling up the overhangs with Klenow fragment. This construct was isolated by digestion with estriction enzymes AviII and ScaI. Vaccinia recombination plasmid pGS62A (Cranage et al.; 1986) is digested with SmaI. The HCV coding sequence with gx leader sequence is ligated into the SmaI site of pGS62A. CVI-cells were infected with wild type Vaccinia strain WR and transfected with pGS62A containing gp 55 coding sequences. (Macket et al., 1984) Recombinant Vaccinia viruses expressing HCV gp55 were isolated.

Metabolic labeling of CVI cells infected with the Vaccinia recombinant virus containing the HCV gp55 gene was performed. HCV gp55 was detected after radio-immuno precipitation with HCV neutralizing monoclonal antibodies, SDS-PAGE and fluorography. Under nonreducing conditions for SDS-PAGE, the disulfide linked HCV gp55 homodimer (apparent molecular weight of about 100 kD) was observed. The migration characteristics were the same as for HCV gp55 precipitated from HCV infected cells.

EXAMPLE 7

Construction of a 44/48 kD Protein Expression Vector

Clone pHCK11 is digested with restriction enzymes DglI and BanI according to standard techniques. The resulting 0.7 kb fragment, located between nucleotide 1115 (TGTTGGC) and 1838 (GTGC) comprising the HCV 44/48 kD protein, is isolated and ligated to synthetic adaptors connecting the 5'BglI restriction site with the BamHI site of the vaccinia recombination vector pGS62A and the 3' BanI site with the EcoRI site of the vaccinia recombination vector. The sequence of the 5'adaptor is (SEQ ID NOS: 8 and 9).

```
5'-GATCCACCATGGGGGCCCTGT-3'

GTGGTACCCCCGGG
```

The sequence of the 3'adaptor is (SEQ ID NOS: 10 and 11)

```
5'-GTGCCTATGCCTGAG-3'

GATACGGACTCTTAA
```

CVI-cells were infected with wild type Vaccinia strain WR and transfected with pGS62A containing the gp 44/48 coding sequences. Recombinant Vaccinia viruses expressing HCV gp 44/48 were isolated.

Metabolic labeling of CVI cells infected with the Vaccinia recombinant virus containing the HCV gp 44/48 gene was performed. HCV gp 44/48 was detected after radio-immuno precipitation with monoclonal antibodies, SDS-PAGE and fluorography. Under nonreducing conditions for SDS-PAGE, the disulfide linked HCV gp 44/48 homodimer (apparent molecular weight of about 100 kD) was observed. The migration characteristics were the same as for HCV gp 44/48 precipitated from HCV infected cells. It was demonstrated that the monoclonal antibodies which precipitated gp 44/48 from cells infected with the Vaccinia recombinant neutralize HCV.

REFERENCES

Figure 1:
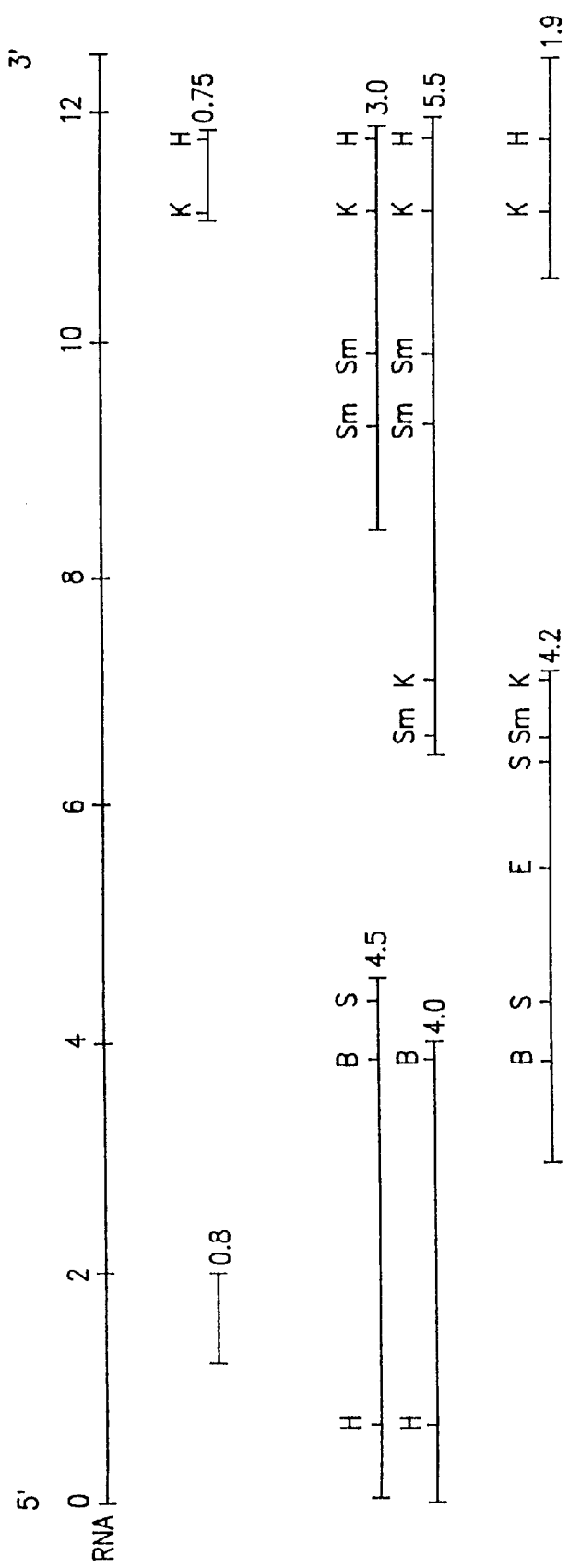
FIG. 1 displays physical maps of different HCV derived cDNA clones and their position relative to the RNA genome (upper line). Two HCV derived cDNA clones isolated after screening with either the antibody probe (0.8 kb clone) or the degenerated oligonucleotide probe (0.75 kb clone) are shown in the second line. The cDNA fragments chosen for nucleotide sequencing are indicated below. All numbers represent sizes of DNA fragments in kb. Restriction sites: B=Bgl II; E=EcoRI; H=Hind III; K=Kpn I; S=Sal I; Sm=Sma I.
Figure 2:
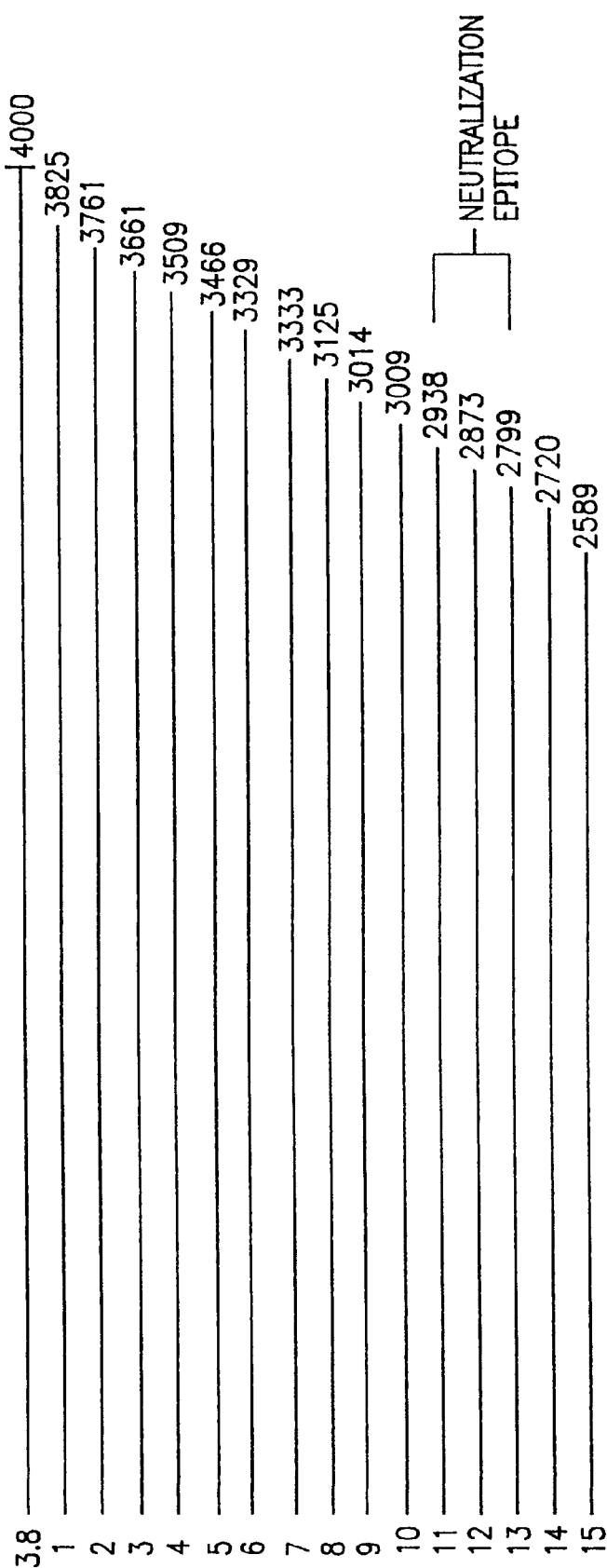
FIG. 2 shows the length of the HCV DNA cloned in the pGS62 vector. A set of 15 deletion mutants derived from cDNA clone pHCK11 was established by treatment with Exonuclease III and cloned in the pGS62 vector giving rise to pGS62-3.8Exo 1–15. 3' end nucleotides are indicated.

BENTON, W., and DAVIS, R. (1977). Screening λgt recombinant clones by hybridization to single plaques in sity. Science 196, 180–182.

CHIRGWIN, J. M., PRZYBYLA, A. E., MAcDONALD, R. J., and RUTTER, W. J. (1979). Isolation of biologically active ribonucleic acid from sources enriched in ribonuclease, Biochemistry 18, 5294–5299.

CRANAGE, M. P. et al. (1986). EMBO, J. 5, 3057–3063.

DAVIS, L. G., DIBNER, M. D., and BATTEY, J. F. (1986). Basic Methods in Molecular Biology, 190–191. Elsevier, New York, Amsterdam, London.

DENTE, L., SOLLAZZO, M., BALDARI, C., CESARENI, G., and CORTESE, R. (1985). The pEMBL family of single-stranded vectors. In: DNA Cloning, Vol. 1, (Glover, D. M., ed.), IRL Press Oxford/Washington D.C., pp. 101–107.

GEYSEN et al., H. M. (1987) J. Immunol. Meth. 102, 259–274.

HENNIKOFF, S. (1987). Unidirectional digestion with exonuclease III in DNA sequence analysis. In: Meth. Enzymol. (Wu, R., ed.) 155, 156–165.

HUYNH, T. V., YOUNG, R. A., and DAVIS, R. W. (1985). Constructing and screening cDNA libraries in λgt10 and λgt11. In: DNA Cloning: A Practical Approach, Vol. 2, (Glover, D. M., ed.), IRL Press Oxford, pp. 49–78.

KEIL, G. M., EBELING-KEIL, A., and KOSZINOWSKI, U. H. (1984). Temporal regulation of murine cytomegalovirus transcription and mapping of viral RNA synthesized at immediate early times after infection, J. Virol. 50, 784–795.

MACKETT, M. et al. (1984) J. Virol. 49, 857–864.

MANIATIS, T., FRITSCH, E. F., and SAMBROOKS, S. (1982). Molecular Cloning, a Laboratory Manual. Cold Spring Harbor Laboratory Press, Cold Spring Harbor, N.Y.

SANGER, F., NICKLEN, S., and COULSON, A. R. (1977). DNA sequencing with chain-terminating inhibitors. Proc. Natl. Acad. Sci. U.S.A. 74, 5363–5467.

MANIATIS, T. et al. (1989). Molecular Cloning, a Laboratory Manual, second edition, Cold Spring Harbor Laboratory Press, Cold Spring Harbor, N.Y.

STREBEL, K. et al. (1986). J. Virology 57, 983–991.

RüMENOPF, T. et al. (1989). Virology 171, 18–27.

YOUNG, R. A., and DAVIS, R. W. (1983). Efficient isolation of genes by using antibody probes. Proc. Natl. Acad. Sci. U.S.A. 80, 1194–1198.

What is claimed is:

1. An isolated hog cholera virus (HCV) protein, which is the 44/48 kD protein.

2. The protein according to claim 1, which comprises the amino acid sequence from about 263–487 of SEQ ID NO: 2.

3. An isolated HCV protein which is expressed by a recombinant nucleic acid molecule comprising a DNA sequence encoding the 44/48 kD protein of HCV.

4. A method for the preparation of an HCV protein, comprising growing a recombinant host cell or recombinant virus comprising a nucleic acid sequence encoding the 44/48 kD protein of HCV, in a culture under conditions whereby the protein is expressed, followed by isolating the 44/48 kD protein from the culture.

5. A vaccine for the protection of animals against HCV infection, comprising a protein according to claim 1.

6. The vaccine according to claim 5, wherein the protein comprises the amino acid sequence from about 263–487 of SEQ ID NO: 2.

7. The vaccine according to claim 5, wherein the protein is recombinantly expressed.

8. A method for the detection of the presence of HCV antibodies in an animal, comprising reacting the 44/48 kD protein of HCV with the serum of the animal, and determining the presence of an antibody/antigen complex, whereby the presence of the complex indicates a positive result.

* * * * *